(12) United States Patent
Lin et al.

(10) Patent No.: US 11,913,053 B2
(45) Date of Patent: Feb. 27, 2024

(54) APPLICATION OF TREHALASE IN FERMENTATIVE PRODUCTION

(71) Applicant: Nanjing Bestzyme Bio-Engineering Co., Ltd., Jiangsu (CN)

(72) Inventors: Jie Lin, Nanjing (CN); Hongxian Xu, Nanjing (CN); Hui Peng, Nanjing (CN)

(73) Assignee: Nanjing Bestzyme Bio-Engineering Co., Ltd., Jiangsu (CN)

( * ) Notice: Subject to any disclaimer, the term of this patent is extended or adjusted under 35 U.S.C. 154(b) by 100 days.

(21) Appl. No.: 17/277,211

(22) PCT Filed: Sep. 17, 2019

(86) PCT No.: PCT/CN2019/106078
§ 371 (c)(1),
(2) Date: Mar. 17, 2021

(87) PCT Pub. No.: WO2020/057476
PCT Pub. Date: Mar. 26, 2020

(65) Prior Publication Data
US 2021/0403957 A1     Dec. 30, 2021

(30) Foreign Application Priority Data
Sep. 17, 2018   (CN) .......................... 201811083590.3

(51) Int. Cl.
C12P 7/06   (2006.01)
C12P 13/08  (2006.01)
C12P 13/14  (2006.01)

(52) U.S. Cl.
CPC ............... *C12P 7/06* (2013.01); *C12P 13/08* (2013.01); *C12P 13/14* (2013.01); *C12Y 302/01028* (2013.01)

(58) Field of Classification Search
CPC .. C12P 7/06; C12P 13/08; C12P 13/14; C12P 13/04; C12P 19/14; C12P 19/02; C12Y 302/01028; Y02E 50/10; C12N 9/24
See application file for complete search history.

(56) References Cited

FOREIGN PATENT DOCUMENTS

| CN | 105722989 A | 6/2016 |
|----|-------------|--------|
| CN | 107058415 A | 8/2017 |
| CN | 108350442 A | 7/2018 |
| CN | 108474010 A | 8/2018 |
| WO | WO 2013/148993 A1 | 10/2013 |
| WO | WO 2015/065978 A1 | 5/2015 |
| WO | WO 2016/205127 | * 12/2016 |
| WO | WO 2018/204798 | * 11/2018 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Guo et al., PNAS 101(25):9205-9210, 2004.*
Berka et al., "Thermothelomyces Thermophilia ATCC 42464 Glycoside Hydrolase Family 37 Protein Partial mRNA, Sequence No. XM_003658344.1," *NCBI_Genbank*, Jun. 12, 2017 (3 pages).
Berka et al., "Thielavia Terrestris NRRL 8126 Glycoside Hydrolase Family 37 Protein mRNA, Sequence No. XM_003656308.1." *NCBI_Genbank*, Jun. 5, 2017 (3 pages).
Han et al., "Application of Trehalase in Glutamic Acid Fermentation," *Guangzhou Chemical Industry*, vol. 45, No. 7, p. 73 (Apr. 30, 2017) (with English abstract only).
Heijne et al., "Rasamsonia Emersonii CBS 394.64 Acid Trehalase mRNA, Sequence No. XM_013476474.1," *NCBI_Genbank*, Aug. 12, 2015 (2 pages).
PCT/CN2019/106078 English translation of International Search Report dated Nov. 28, 2019 (4 pages).
PCT/CN2019/106078 International Search Report and Written Opinion dated Nov. 28, 2019 (8 pages).
Barraza et al., "Trehalases: A neglected carbon metabolism regulator?" *Plant Signaling & Behavior*, 8(7):e24778-1-e24778-5 (Jul. 2013).

* cited by examiner

*Primary Examiner* — Delia M Ramirez
(74) *Attorney, Agent, or Firm* — Klarquist Sparkman, LLP

(57) ABSTRACT

Provided is an application of trehalase in fermentative production. The trehalase has amino acid sequences shown in SEQ ID NO.6, SEQ ID NO.7, and SEQ ID NO.8. Provided are methods for producing and applying trehalase, particularly being applied in the production and fermentation of alcohol and an amino acid.

20 Claims, 5 Drawing Sheets
Specification includes a Sequence Listing.

SEQUENCE LISTING

<160> NUMBER OF SEQ ID NOS: 22

<210> SEQ ID NO 1
<211> LENGTH: 2724
<212> TYPE: DNA
<213> ORGANISM: Artificial Sequence
<220> FEATURE:
<223> OTHER INFORMATION: amdS expression cassette

<400> SEQUENCE: 1

| | | | | | |
|---|---|---|---|---|---|
| ctagatctac | gccaggaccg | agcaagccca | gatgagaacc | gacgcagatt | tccttggcac | 60 |
| ctgttgcttc | agctgaatcc | tggcaatacg | agatacctgc | tttgaatatt | ttgaatagct | 120 |
| cgcccgctgg | agagcatcct | gaatgcaagt | aacaaccgta | gaggctgaca | cggcaggtgt | 180 |
| tgctagggag | cgtcgtgttc | tacaaggcca | gacgtcttcg | cggttgatat | atatgtatgt | 240 |
| ttgactgcag | gctgctcagc | gacgacagtc | aagttcgccc | tcgctgcttg | tgcaataatc | 300 |
| gcagtgggga | agccacaccg | tgactcccat | ctttcagtaa | agctctgttg | gtgtttatca | 360 |
| gcaatacacg | taatttaaac | tcgttagcat | ggggctgata | gcttaattac | cgtttaccag | 420 |
| tgccgcggtt | ctgcagcttt | ccttggcccg | taaaattcgg | cgaagccagc | caatcaccag | 480 |
| ctaggcacca | gctaaaccct | ataattagtc | tcttatcaac | accatccgct | ccccgggat | 540 |
| caatgaggag | aatgaggggg | atgcgggget | aaagaagcct | acataaccct | catgccaact | 600 |
| cccagtttac | actcgtcgag | ccaacatcct | gactataagc | taacacagaa | tgcctcaatc | 660 |
| ctgggaagaa | ctgccgctg | ataagcgcgc | ccgcctcgca | aaaccatcc | ctgatgaatg | 720 |
| gaaagtccag | acgctgcctg | cggaagacag | cgttattgat | ttcccaaaga | aatcggggat | 780 |
| cctttcagag | gccgaactga | agatcacaga | ggcctccgct | gcagatcttg | tgtccaagct | 840 |
| ggcggccgga | gagttgacct | cggtggaagt | tacgctagca | ttctgtaaac | gggcagcaat | 900 |
| cgcccagcag | ttagtagggt | cccctctacc | tctcagggag | atgtaacaac | gccaccttat | 960 |
| gggactatca | agctgacgct | ggcttctgtg | cagacaaact | gcgcccacga | gttcttccct | 1020 |
| gacgccgctc | tcgcgcaggc | aagggaactc | gatgaatact | acgcaaagca | caagagaccc | 1080 |
| gttggtccac | tccatggcct | ccccatctct | ctcaaagacc | agcttcgagt | caaggtacac | 1140 |
| cgttgcccct | aagtcgttag | atgtcccttt | ttgtcagcta | acatatgcca | ccagggctac | 1200 |
| gaaacatcaa | tgggctacat | ctcatggcta | aacaagtacg | acgaagggga | ctcggttctg | 1260 |
| acaaccatgc | tccgcaaagc | cggtgccgtc | ttctacgtca | agacctctgt | cccgcagacc | 1320 |
| ctgatggtct | gcgagacagt | caacaacatc | atcgggcgca | ccgtcaaccc | acgcaacaag | 1380 |
| aactggtcgt | gcgcggcag | ttctggtggt | gagggtgcga | tcgttgggat | tcgtggtggc | 1440 |
| gtcatcggtg | taggaacgga | tatcggtggc | tcgattcgag | tgccggccgc | gttcaacttc | 1500 |
| ctgtacggtc | taaggccgag | tcatgggcgg | ctgccgtatg | caaagatggc | gaacagcatg | 1560 |
| gagggtcagg | agacggtgca | cagcgttgtc | gggccgatta | cgcactctgt | tgagggtgag | 1620 |
| tccttcgcct | cttccttctt | ttcctgctct | ataccaggcc | tccactgtcc | tcctttcttg | 1680 |
| cttttatac | tatatacgag | accggcagtc | actgatgaag | tatgttagac | ctccgcctct | 1740 |
| tcaccaaatc | cgtcctcggt | caggagccat | ggaaatacga | ctccaaggtc | atccccatgc | 1800 |
| cctggcgcca | gtccgagtcg | acattattg | cctccaagat | caagaacggc | gggctcaata | 1860 |
| tcggctacta | caacttcgac | ggcaatgtc | ttccacaccc | tcctatcctg | cgcggcgtgg | 1920 |
| aaaccaccgt | cgccgcactc | gccaaagccg | gtcacaccgt | gaccccgtgg | acgccataca | 1980 |
| agcacgattt | cggccacgat | ctcatctccc | atatctacgc | ggctgacggc | agcgccgacg | 2040 |

```
taatgcgcga tatcagtgca tccggcgagc cggcgattcc aaatatcaaa gacctactga    2100
acccgaacat caaagctgtt aacatgaacg agctctggga cacgcatctc cagaagtgga    2160
attaccagat ggagtacctt gagaaatggc gggaggctga agaaaaggcc gggaaggaac    2220
tggacgccat catcgcgccg attacgccta ccgctgcggt acggcatgac cagttccggt    2280
actatgggta tgcctctgtg atcaacctgc tggatttcac gagcgtggtt gttccggtta    2340
cctttgcgga taagaacatc gataagaaga atgagagttt caaggcggtt agtgagcttg    2400
atgccctcgt gcaggaagag tatgatccgg aggcgtacca tggggcaccg gttgcagtgc    2460
aggttatcgg acggagactc agtgaagaga ggacgttggc gattgcagag gaagtgggga    2520
agttgctggg aaatgtggtg actccatagc taataagtgt cagatagcaa tttgcacaag    2580
aaatcaatac cagcaactgt aaataagcgc tgaagtgacc atgccatgct acgaaagagc    2640
agaaaaaaac ctgccgtaga accgaagaga tatgacacgc ttccatctct caaaggaaga    2700
atcccttcag ggttgcgttt ccag                                           2724

<210> SEQ ID NO 2
<211> LENGTH: 997
<212> TYPE: DNA
<213> ORGANISM: Artificial Sequence
<220> FEATURE:
<223> OTHER INFORMATION: DNA fragments containing the gla promoter and
      terminator of an Aspergillus niger saccharifying enzyme gene

<400> SEQUENCE: 2
gccattggcg gaggggtccg gacggtcagg aacttagcct tatgagatga atgatggacg     60
tgtctggcct cggaaaagga tatatgggga tcatgatagt actagccata ttaatgaagg    120
gcatatacca cgcgttggac ctgcgttata gcttcccgtt agttatagta ccatcgttat    180
accagccaat caagtcacca cgcacgaccg gggacggcga atccccggga attgaaagaa    240
attgcatccc aggccagtga ggccagcgat tggccacctc tccaaggcac agggccattc    300
tgcagcgctg gtggattcat cgcaatttcc cccggcccgg cccgacaccg ctataggctg    360
gttctcccac accatcggag attcgtcgcc taatgtctcg tccgttcaca agctgaagag    420
cttgaagtgg cgagatgtct ctgcaggaat tcaagctaga tgctaagcga tattgcatgg    480
caatatgtgt tgatgcatgt gcttcttcct tcagcttccc ctcgtgcaga tgaggtttgg    540
ctataaattg aagtggttgg tcggggttcc gtgaggggct gaagtgcttc ctcccttttta   600 gacgcaactg agagcctgag cttcatcccc agcatcatta cacctcagca cttaagacta    660
gtacgcgtct cgagatctag agggtgactg acacctggcg gtagacaatc aatccatttc    720
gctatagtta aaggatgggg atgagggcaa ttggttatat gatcatgtat gtagtgggtg    780
tgcataatag tagtgaaatg gaagccaagt catgtgattg taatcgaccg acggaattga    840
ggatatccgg aaatacagac accgtgaaag ccatggtctt tccttcgtgt agaagaccag    900
acagacagtc cctgatttac ccttgcacaa agcactagaa aattagcatt ccatccttct    960
ctgcttgctc tgctgatatc actgtcattc aatgcat                             997

<210> SEQ ID NO 3
<211> LENGTH: 2088
<212> TYPE: DNA
<213> ORGANISM: Artificial Sequence
<220> FEATURE:
<223> OTHER INFORMATION: Thi37

<400> SEQUENCE: 3
```

```
atggccccc gctccttcgt cgccgccgcc gccctcgccg gtctcatctc ctccgcctcc        60
gccctctaca tcaacggttc cgtcaccgcc ccctgcgact ccccccctcta ctgccacggt       120 gagatcctca aggccatcga gctcgcccac cccttcaccg actccaagac cttcgtcgac       180
atgcccacca tccgccccct cgacgaggtc atcgccgcct caaccgcct ctcccagccc        240 ctctccaaca actccgagct caacgccttc ctcgccgcca acttcgcccc gccggtggt        300 gagctcgagg ccgtccccg cgaccagctc cacaccgagc cctccttcct caacaagctc       360
gacgacaccg tcatcaagga gttcgtcgcc aaggtcatcg acatctggcc cgacctcacc       420
cgccgctacg tggtcccgg taactgcacc gcctgcgcca actccttcat ccccgtcaac       480
cgcaccttcg tcgtcgccgg tggtcgcttc cgcgagccct actactggga ctcctactgg       540
atcctcgagg gtctcctccg caccggtggt gccttcaccg agatctccaa gaacatcatc       600
gagaacttcc tcgacttcgt cgagaccatc ggtttcatcc caacggtgc ccgcatctac       660 tacctcgacc gctcccagcc ccccctcctc gccgcatgg tccgctccta cgtcgactac       720
accaacgaca cctccatcct cgaccgcgcc ctccccctcc tcatcaagga gcacgagttc       780
tggtccacca accgctccgt ctccatcaag gcccccaacg gtaagaccta cacccctcaac      840 cgctactacg tcaacaacaa ccagccccgc cccgagtcct tccgcgagga ctacatcacc       900
gccaacaacg gttcctacta cgccgcctcc ggtatcatct accccgtcaa cacccccctc       960
aacgacaccg agaaggccga gctctacgcc aacctcgcct ccggtgccga gaccggttgg      1020
gactactcca cccgctggct caagaacccc aacgacgccg ccaaggacat ctacttcccc      1080
ctccgctccc tcaacgtccg cggtaccgtc cccgtcgacc tcaactccat cctctacgag      1140
aacgaggtca tcatctccca gtacctcaag cgcgccggta caactccga ggccgagcgc      1200 tgggcctacg ccgcctccca cgcgctccgag gccatgttcg agctcatgtg aacgccacc      1260 cactggtcct acttcgacta caacctcacc tccaactccc agcgcatctt cgtccccgtc      1320
gacgacgacg ccaccgccgc cgagcgcgcc ggtgcccccc gcggtcagca ggtcctcttc      1380
aacatcggtc agttctaccc cttctggacc ggtgccgccc cgcccagct caagaacaac       1440 cccctcgccg tccagcaggc ctacgcccgc gtcgcccgca tgctcgacga aacgccggt      1500 ggtatccccg ccaccaactt cgtcaccggt cagcagtggg accagcccaa cgtctggccc      1560
cccctccagc acgtcctcat ggagggtctc ctcaacaccc cccccaccttt cggtgacgcc      1620 gaccccgcct accagtccgt ccgcgccctc gccctccgcc tcgcccagcg ctacctcgac      1680
tccaccttct gcacctggta cgccaccggt ggttccacct cccagacccc ccagctccag      1740
ggtgtcgccc ccggtgccga gggtatcatg ttcgagaagt acgccgacaa ctccaccaac      1800
gtcgccggtt ccggtggtga gtacgaggtc gtcgagggtt cggttggtc caacggtgtc      1860 ctcatctggg ccgccgacgt cttcggtgcc cagctcaagc ccccgactg cggtaacatc      1920 accgccgccc acacctccgg ttccggtgcc cagaagcgct ccggtggttc cctcgcccgc      1980
cgcgccgtcg agctcgaccc ctgggacgcc gcctggacca agatgttcgg tcgctccgcc      2040
ctcaagaagc gcgaggacgt ccgcaagcgc tggctcctcg ccgcctaa                    2088
```

<210> SEQ ID NO 4
<211> LENGTH: 2085
<212> TYPE: DNA
<213> ORGANISM: Artificial Sequence
<220> FEATURE:
<223> OTHER INFORMATION: Myc37

<400> SEQUENCE: 4

```
atggccctcc gccacgccgc caccgccgcc ctcgccggtc tctcctcctc cgccgccgcc      60
ctctacatca acggttccgt caccgccccc tgcgactccc ccatctactg ccacggtgag     120
ctcctcaagg gtgtcgagct cgcccacccc ttcgtcgact ccaagacctt cgtcgacatg     180
cccacccrca agcccgtcga cgaggtcctc gccgccttct ccaagctccg ccagcccctc     240
tccaacaact ccgagctcaa caacttcctc gccgagtact ccgccccgc cggtcacgag      300
ctcgaggagg tccccaaggg tgagctccag atcgacccca agttcctcaa caagctcgag     360
gaccgcacca tcaaggagtt cgtctccaag gtcatcgaca tctggcccga cctcacccgc     420
cgctacgccg gtcccggtga ctgctccggt tgcgccaact ccttcatccc cgtcaaccgc     480
accttcgtcg tcgccggtgg tcgcttccgc gagcccrtact actgggactc ctactggatc     540
ctcgagggtc tcctccgcac cggtggtgcc ttcacccaga tctccaagaa catcatcgag     600
aacttcctcg acttcatcga caccatcggt ttcatcccca cggtgcccg catctactac      660
ctcaaccgct cccagccccc cctcctcacc cgcatggtca agtcctacgt cgactacacc     720
aacgacacct ccatcctcga gcgcgccctc cccctcctca tcaaggagca cgacttcttc     780
accaacaacc gctccgtctc cgtcaccgcc tccaacggta gacctacac cctcaccgc      840
taccacgtcg agaacaacca gccccgcccc gagtcctacc gcgaggacta catcaccgcc     900
aacaacggtt cctactacgc cgcctccggt atcatctacc ccgtcaagac cccccrcaac    960
gagaccgaga aggccgtcct ctactccaac ctcgcctccg gtgccgagtc cggttgggac    1020
tacaccgccc gctggctccg cgtccccgac gacgccgccc gcgacgtcta cttccccctc    1080
cgctcccrca acgtccgcga gatggtcccc gtcgacctca actccatcct ctacgagaac    1140
gaggtcatca tcgccgagta cctcgagaag gccggtaact cctccgaggc caagcgcttc    1200
gcctccgccg ccaagcagcg ctccgaggcc atgtacaacc tcatgtggaa cgccacccac    1260
tggtcctact tcgactacaa cctcacctcc aacgcccaga acatcttcgt ccccgccgac    1320
gaggacaccg cctccttcga ccgctacgcc gcccccccg gtcagcaggt cctcttccac     1380
gtcgcccagc tctaccccrtt ctggaccggt gccgccccrg cccacctcaa gtccaaccrc    1440
ctcgccgtcc agaaggccta cgcccgcgtc tcccgccgcc tcgacaccaa gaagggtgcc    1500
atcgccgcca ccaactaccg caccggtcag cagtgggacc agcccaacgt ctggcccccc    1560
ctccagcacg tcctcatgca gggtctcctc aacacccccg ccaccttcgg tgagtccgac    1620
cccgcctacc agggtgtcca gaagctcgcc ctcgcctcg cccagcgcta cctcgactcc     1680
accttctgca cctggtacgc caccggtggt tccacctccg acttccccca gctccagggt    1740
gtctcccccg acgccaccgg tatcatgttc gagaagtacg ccgactccgc caccaacgtc    1800
gccggtggtg gtggtgagta cgaggtcgtc gagggtttcg gttggaccaa cggtgtcctc    1860
atctggcccg ccgacgtctt cggtaacaag ctcaagcgcc ccgactgcgg taacatcacc    1920
gccgcccaca cccactccga ggccaagcgc tccctcggtg acggtggtct cgcccgccgc    1980
gccgtcgagc tcgaccccrtg gacgccgcc tggaccaaga tgttcggtcg ctccaagctc    2040
cgccgccgcg aggccgagga cgtccgcaag cgctggtcct cctaa                    2085
```

<210> SEQ ID NO 5
<211> LENGTH: 3204
<212> TYPE: DNA
<213> ORGANISM: Artificial Sequence
<220> FEATURE:
<223> OTHER INFORMATION: Tem65

<400> SEQUENCE: 5

| | | | | | |
|---|---|---|---|---|---|
| atgcaatcga | agttgttgtc | cctgctgctc | ctgtcactcc | ctgcgtcatg | cctcccctg | 60 |
| gaagaacggg | tcgcccaagt | tgtccgagct | tacagccgcc | cccacggcct | gcaggtccgc | 120 |
| gacggcaacc | ctggtaacgc | ctcccagacc | tacgaaaccc | gattccctgg | tgtgacctgg | 180 |
| gaccagcaca | actggcgcct | gacctccacc | gtcctcgatc | agggccatta | ccagagccgc | 240 |
| ggttccatcg | ccaacggcta | cgtcggtatc | aacgtggcta | cgctggtcc | gttcttcgag | 300 |
| ctggacaccc | ccgtcgatgg | cgacgtgatc | aacggttggc | ctctcttctc | ccgccgccag | 360 |
| accttcgcta | ccatcgctgg | cttctacgat | gagcagcccc | gcaccaacgg | taccaacttc | 420 |
| ccttggctgt | accagtacgg | tggcgagagc | gtcatctccg | gtgtgcctca | ctggtccggc | 480 |
| ctggtcctgg | atctcggcga | cggtaactac | ctggatgcta | ccgtcgactc | cagcaccatc | 540 |
| agcgattact | ccaccgtgta | cgactacaag | gccggcatcc | tcagctggtc | ctacacctgg | 600 |
| accccgaagg | gcaacaaggg | tagcttcaag | atcaactact | ccctgttcgc | tcataagctc | 660 |
| tacgtgaacc | aggctgtcgt | gcgcctcgac | atcaccccctt | ccaccaacac | caacgctacc | 720 |
| gtcgtgaacc | tcatcgatgg | ctacagcgct | gtccgaaccg | acttcgtggg | ttccggcaag | 780 |
| gatggcgacg | ctatctacag | cgccgtgcgc | ccttggggta | tctccaacgt | gaccgcttac | 840 |
| atctacaccg | tcctggatgg | ctccaacggt | gtggacctct | ccagtccgc | catcgtcaac | 900 |
| aacaagccgt | acatccacac | caacgatagc | tccatcgctc | aggccgtcaa | cgtgggcttc | 960 |
| cgctccggta | agaccgtcac | catcaccaag | ttcgtgggtg | ctgctagctc | cgatgctttc | 1020 |
| cctaacccgc | agcagaccgc | taaggacgcc | gctctcaccg | ccaagaagaa | gggttacgat | 1080 |
| gctctgctcc | acagccatgt | cgctgagtgg | gctgctgtga | tgcctgacga | gtccgtcgat | 1140 |
| gacttcacct | tccctgagaa | cggtaccctg | cctcaggatc | ctttcatcat | cgagagcgct | 1200 |
| atcaccgccg | tcgtgaaccc | ttactacctg | ctccagaaca | ccgtcggcga | gaacgctctc | 1260 |
| aaggagatct | ccaacgcccc | ggtcaacgag | tggagcatct | ccgtgggcgg | tctgaccagc | 1320 |
| gactcctacg | ctggcctcat | cttctgggat | gccgacctgt | ggatgcatcc | tggcctggcc | 1380 |
| gctgctttcc | ctaaggctgc | tcagcgaatc | cctaactacc | gcgtcgctaa | gtaccagcag | 1440 |
| gctcgccgca | acgtcaagac | cgccttcacc | agctccaaga | acgaaacctg | gttcagcgac | 1500 |
| tccgctgctg | tgtaccccttg | gacctccggt | cgatacggta | actgcaccgg | taccggtcct | 1560 |
| tgctgggatt | acgagtacca | cctgaacggc | gacatcggtc | tgagcctcat | caaccagtgg | 1620 |
| gtcgcctccg | gcgataccaa | gaccttccag | gagagctact | ccctatcta | cgattccatc | 1680 |
| gctaccctgt | acgccgacct | gctccagcct | aacggtaccc | attggaccct | caccaacatg | 1740 |
| accgatccgg | acgagtacgc | taacgccgtc | gatgccggcg | gttacaccat | gccgctgatc | 1800 |
| gctcagaccc | tgctctacgc | caacagcttc | cgcaagcagt | tcggcatcca | gcagaacaac | 1860 |
| acctggacca | catggcttc | caacatcctg | ctcctgcgcg | agaacgatgt | gacccctcgag | 1920 |
| tacaccacca | tgaacaacag | cgtccaggtg | aagcaggccg | atgtcgtgct | ggtcacctac | 1980 |
| cccctcgact | acacctccaa | ctacagctcc | accgatgctc | tggatgaccct | cgactactac | 2040 |
| gctctcaagc | agagccctga | cggtcctggt | atgacctacg | ctatcttctc | catcgtcgcc | 2100 |
| aacgaggtga | gcccttccgg | ctgcagcgtc | tacacctacg | ctcagtactc | ctacgatcct | 2160 |
| tacgtgcgcg | ccccgttctt | ccagttctcc | gagcagctgg | tcgatgacta | cacccctcaac | 2220 |
| ggcggtaccc | accctgctta | cccgttcctg | accggccatg | gcggtgccaa | ccaggtcgtg | 2280 |

-continued

```
atctacggtt acctgggcct gcgcctgctg cctgatgacg tcatccacat cgaccctaac    2340
ctcccccctc aggtcccgca tgtgaagtac cgcaccttct actggcgagg ttggcctatc    2400
caggccagct ccaactacac ccacaccacc ctgcgccgcg ctgctcatgt gcaggctctc    2460
gataccgccg accagcgctt cgctaagacc gccatccctg tccaagtggg tagcggcaag    2520
aacgtcaccg tgtaccagct gcctgtcaac ggtcagctca ccgtccctaa ccgacaagtg    2580
ggttccaagc tgaccgtccc tggtaacctc gctcagtgcc agcctgtgca gagccaggac    2640
tcctacgagc tggccagta ccctatggct gctgtggatg gtgctgcctc caccaagtgg    2700
cagccgagct ccgctgccaa caccagctcc ctgaccgtca gcctccccca gagcgagtcc    2760
ggtaccatgg tgtccggttt ctacttcgat tgggctcagg ctcctcctgt gaacgctacc    2820
gtcgtgttcc ataacgatac cagcgaggac ccctgagcg cttccgctgg tggccagtac    2880
ttcgtcacca acatcaacaa catcaccctc agctcccccct acaaccctca ggccaactcc    2940
gctgacgcca tcatgctgcc tagctccaac accaccaacg tcaccctcgc tcagcctgtc    3000
cctgtgcctc gctacgccac cctgtacatc accggcaacc aggctctcag cgagtccgat    3060
gtccaggctc agaacggtac cggtgctacc gtggctgagt gggctatcct ggctagcaac    3120
cctcaggctg gtttccccttc cgagaagagt cgctgtgaag catcggtggc acgcctgtgg    3180
ctggattgta tgttgggtgg gtaa                                            3204
```

<210> SEQ ID NO 6
<211> LENGTH: 695
<212> TYPE: PRT
<213> ORGANISM: Artificial Sequence
<220> FEATURE:
<223> OTHER INFORMATION: THI37

<400> SEQUENCE: 6

```
Met Ala Pro Arg Ser Phe Val Ala Ala Ala Leu Ala Gly Leu Ile
1               5                   10                  15

Ser Ser Ala Ser Ala Leu Tyr Ile Asn Gly Ser Val Thr Ala Pro Cys
            20                  25                  30

Asp Ser Pro Leu Tyr Cys His Gly Glu Ile Leu Lys Ala Ile Glu Leu
        35                  40                  45

Ala His Pro Phe Thr Asp Ser Lys Thr Phe Val Asp Met Pro Thr Ile
    50                  55                  60

Arg Pro Leu Asp Glu Val Ile Ala Ala Phe Asn Arg Leu Ser Gln Pro
65                  70                  75                  80

Leu Ser Asn Asn Ser Glu Leu Asn Ala Phe Leu Ala Ala Asn Phe Ala
                85                  90                  95

Pro Ala Gly Gly Glu Leu Glu Ala Val Pro Arg Asp Gln Leu His Thr
            100                 105                 110

Glu Pro Ser Phe Leu Asn Lys Leu Asp Asp Thr Val Ile Lys Glu Phe
        115                 120                 125

Val Ala Lys Val Ile Asp Ile Trp Pro Asp Leu Thr Arg Arg Tyr Gly
    130                 135                 140

Gly Pro Gly Asn Cys Thr Ala Cys Ala Asn Ser Phe Ile Pro Val Asn
145                 150                 155                 160

Arg Thr Phe Val Val Ala Gly Gly Arg Phe Arg Glu Pro Tyr Tyr Trp
                165                 170                 175

Asp Ser Tyr Trp Ile Leu Glu Gly Leu Leu Arg Thr Gly Gly Ala Phe
            180                 185                 190

Thr Glu Ile Ser Lys Asn Ile Ile Glu Asn Phe Leu Asp Phe Val Glu
```

```
            195                 200                 205
Thr Ile Gly Phe Ile Pro Asn Gly Ala Arg Ile Tyr Tyr Leu Asp Arg
210                 215                 220

Ser Gln Pro Pro Leu Leu Ala Arg Met Val Arg Ser Tyr Val Asp Tyr
225                 230                 235                 240

Thr Asn Asp Thr Ser Ile Leu Asp Arg Ala Leu Pro Leu Leu Ile Lys
                245                 250                 255

Glu His Glu Phe Trp Ser Thr Asn Arg Ser Val Ser Ile Lys Ala Pro
                260                 265                 270

Asn Gly Lys Thr Tyr Thr Leu Asn Arg Tyr Tyr Val Asn Asn Asn Gln
            275                 280                 285

Pro Arg Pro Glu Ser Phe Arg Glu Asp Tyr Ile Thr Ala Asn Asn Gly
            290                 295                 300

Ser Tyr Tyr Ala Ala Ser Gly Ile Ile Tyr Pro Val Asn Thr Pro Leu
305                 310                 315                 320

Asn Asp Thr Glu Lys Ala Glu Leu Tyr Ala Asn Leu Ala Ser Gly Ala
                325                 330                 335

Glu Thr Gly Trp Asp Tyr Ser Thr Arg Trp Leu Lys Asn Pro Asn Asp
                340                 345                 350

Ala Ala Lys Asp Ile Tyr Phe Pro Leu Arg Ser Leu Asn Val Arg Gly
            355                 360                 365

Thr Val Pro Val Asp Leu Asn Ser Ile Leu Tyr Glu Asn Glu Val Ile
370                 375                 380

Ile Ser Gln Tyr Leu Lys Arg Ala Gly Asn Asn Ser Glu Ala Glu Arg
385                 390                 395                 400

Trp Ala Tyr Ala Ala Ser Gln Arg Ser Glu Ala Met Phe Glu Leu Met
                405                 410                 415

Trp Asn Ala Thr His Trp Ser Tyr Phe Asp Tyr Asn Leu Thr Ser Asn
            420                 425                 430

Ser Gln Arg Ile Phe Val Pro Val Asp Asp Ala Thr Ala Ala Glu
            435                 440                 445

Arg Ala Gly Ala Pro Arg Gly Gln Gln Val Leu Phe Asn Ile Gly Gln
450                 455                 460

Phe Tyr Pro Phe Trp Thr Gly Ala Ala Pro Ala Gln Leu Lys Asn Asn
465                 470                 475                 480

Pro Leu Ala Val Gln Gln Ala Tyr Ala Arg Val Ala Arg Met Leu Asp
                485                 490                 495

Glu Asn Ala Gly Gly Ile Pro Ala Thr Asn Phe Val Thr Gly Gln Gln
                500                 505                 510

Trp Asp Gln Pro Asn Val Trp Pro Pro Leu Gln His Val Leu Met Glu
            515                 520                 525

Gly Leu Leu Asn Thr Pro Pro Thr Phe Gly Asp Ala Asp Pro Ala Tyr
            530                 535                 540

Gln Ser Val Arg Ala Leu Ala Leu Arg Leu Ala Gln Arg Tyr Leu Asp
545                 550                 555                 560

Ser Thr Phe Cys Thr Trp Tyr Ala Thr Gly Gly Ser Thr Ser Gln Thr
                565                 570                 575

Pro Gln Leu Gln Gly Val Ala Pro Gly Ala Glu Gly Ile Met Phe Glu
            580                 585                 590

Lys Tyr Ala Asp Asn Ser Thr Asn Val Ala Gly Ser Gly Gly Glu Tyr
            595                 600                 605

Glu Val Val Glu Gly Phe Gly Trp Ser Asn Gly Val Leu Ile Trp Ala
610                 615                 620
```

-continued

Ala Asp Val Phe Gly Ala Gln Leu Lys Arg Pro Asp Cys Gly Asn Ile
625                 630                 635                 640

Thr Ala Ala His Thr Ser Gly Ser Gly Ala Gln Lys Arg Ser Gly Gly
            645                 650                 655

Ser Leu Ala Arg Arg Ala Val Glu Leu Asp Pro Trp Asp Ala Ala Trp
            660                 665                 670

Thr Lys Met Phe Gly Arg Ser Ala Leu Lys Lys Arg Glu Asp Val Arg
        675                 680                 685

Lys Arg Trp Leu Leu Ala Ala
690                 695

<210> SEQ ID NO 7
<211> LENGTH: 694
<212> TYPE: PRT
<213> ORGANISM: Artificial Sequence
<220> FEATURE:
<223> OTHER INFORMATION: MYC37

<400> SEQUENCE: 7

Met Ala Leu Arg His Ala Ala Thr Ala Ala Leu Ala Gly Leu Ser Ser
1               5                   10                  15

Ser Ala Ala Ala Leu Tyr Ile Asn Gly Ser Val Thr Ala Pro Cys Asp
            20                  25                  30

Ser Pro Ile Tyr Cys His Gly Glu Leu Leu Lys Gly Val Glu Leu Ala
        35                  40                  45

His Pro Phe Val Asp Ser Lys Thr Phe Val Asp Met Pro Thr Leu Lys
    50                  55                  60

Pro Val Asp Glu Val Leu Ala Ala Phe Ser Lys Leu Arg Gln Pro Leu
65                  70                  75                  80

Ser Asn Asn Ser Glu Leu Asn Asn Phe Leu Ala Glu Tyr Phe Ala Pro
                85                  90                  95

Ala Gly His Glu Leu Glu Glu Val Pro Lys Gly Glu Leu Gln Ile Asp
            100                 105                 110

Pro Lys Phe Leu Asn Lys Leu Glu Asp Arg Thr Ile Lys Glu Phe Val
        115                 120                 125

Ser Lys Val Ile Asp Ile Trp Pro Asp Leu Thr Arg Arg Tyr Ala Gly
    130                 135                 140

Pro Gly Asp Cys Ser Gly Cys Ala Asn Ser Phe Ile Pro Val Asn Arg
145                 150                 155                 160

Thr Phe Val Val Ala Gly Gly Arg Phe Arg Glu Pro Tyr Tyr Trp Asp
                165                 170                 175

Ser Tyr Trp Ile Leu Glu Gly Leu Leu Arg Thr Gly Gly Ala Phe Thr
            180                 185                 190

Gln Ile Ser Lys Asn Ile Ile Glu Asn Phe Leu Asp Phe Ile Asp Thr
        195                 200                 205

Ile Gly Phe Ile Pro Asn Gly Ala Arg Ile Tyr Tyr Leu Asn Arg Ser
    210                 215                 220

Gln Pro Pro Leu Leu Thr Arg Met Val Lys Ser Tyr Val Asp Tyr Thr
225                 230                 235                 240

Asn Asp Thr Ser Ile Leu Glu Arg Ala Leu Pro Leu Leu Ile Lys Glu
                245                 250                 255

His Asp Phe Phe Thr Asn Asn Arg Ser Val Ser Val Thr Ala Ser Asn
            260                 265                 270

Gly Lys Thr Tyr Thr Leu His Arg Tyr His Val Glu Asn Asn Gln Pro
        275                 280                 285

```
Arg Pro Glu Ser Tyr Arg Glu Asp Tyr Ile Thr Ala Asn Asn Gly Ser
    290                 295                 300

Tyr Tyr Ala Ala Ser Gly Ile Ile Tyr Pro Val Lys Thr Pro Leu Asn
305                 310                 315                 320

Glu Thr Glu Lys Ala Val Leu Tyr Ser Asn Leu Ala Ser Gly Ala Glu
                325                 330                 335

Ser Gly Trp Asp Tyr Thr Ala Arg Trp Leu Arg Val Pro Asp Asp Ala
            340                 345                 350

Ala Arg Asp Val Tyr Phe Pro Leu Arg Ser Leu Asn Val Arg Glu Met
        355                 360                 365

Val Pro Val Asp Leu Asn Ser Ile Leu Tyr Glu Asn Glu Val Ile Ile
    370                 375                 380

Ala Glu Tyr Leu Glu Lys Ala Gly Asn Ser Ser Glu Ala Lys Arg Phe
385                 390                 395                 400

Ala Ser Ala Ala Lys Gln Arg Ser Glu Ala Met Tyr Asn Leu Met Trp
                405                 410                 415

Asn Ala Thr His Trp Ser Tyr Phe Asp Tyr Asn Leu Thr Ser Asn Ala
            420                 425                 430

Gln Asn Ile Phe Val Pro Ala Asp Glu Asp Thr Ala Ser Phe Asp Arg
        435                 440                 445

Tyr Ala Ala Pro Pro Gly Gln Gln Val Leu Phe His Val Ala Gln Leu
    450                 455                 460

Tyr Pro Phe Trp Thr Gly Ala Ala Pro Ala His Leu Lys Ser Asn Pro
465                 470                 475                 480

Leu Ala Val Gln Lys Ala Tyr Ala Arg Val Ser Arg Leu Asp Thr
                485                 490                 495

Lys Lys Gly Ala Ile Ala Ala Thr Asn Tyr Arg Thr Gly Gln Gln Trp
            500                 505                 510

Asp Gln Pro Asn Val Trp Pro Pro Leu Gln His Val Leu Met Gln Gly
        515                 520                 525

Leu Leu Asn Thr Pro Ala Thr Phe Gly Glu Ser Asp Pro Ala Tyr Gln
    530                 535                 540

Gly Val Gln Lys Leu Ala Leu Arg Leu Ala Gln Arg Tyr Leu Asp Ser
545                 550                 555                 560

Thr Phe Cys Thr Trp Tyr Ala Thr Gly Gly Ser Thr Ser Asp Phe Pro
                565                 570                 575

Gln Leu Gln Gly Val Ser Pro Asp Ala Thr Gly Ile Met Phe Glu Lys
            580                 585                 590

Tyr Ala Asp Ser Ala Thr Asn Val Ala Gly Gly Gly Glu Tyr Glu
        595                 600                 605

Val Val Glu Gly Phe Gly Trp Thr Asn Gly Val Leu Ile Trp Ala Ala
    610                 615                 620

Asp Val Phe Gly Asn Lys Leu Lys Arg Pro Asp Cys Gly Asn Ile Thr
625                 630                 635                 640

Ala Ala His Thr His Ser Glu Ala Lys Arg Ser Leu Gly Asp Gly Gly
                645                 650                 655

Leu Ala Arg Arg Ala Val Glu Leu Asp Pro Trp Asp Ala Ala Trp Thr
            660                 665                 670

Lys Met Phe Gly Arg Ser Lys Leu Arg Arg Arg Glu Ala Glu Asp Val
        675                 680                 685

Arg Lys Arg Trp Ser Ser
    690
```

<210> SEQ ID NO 8
<211> LENGTH: 1067
<212> TYPE: PRT
<213> ORGANISM: Artificial Sequence
<220> FEATURE:
<223> OTHER INFORMATION: TEM65

<400> SEQUENCE: 8

```
Met Gln Ser Lys Leu Leu Ser Leu Leu Leu Ser Leu Pro Ala Ser
1               5                   10                  15

Cys Leu Pro Leu Glu Glu Arg Val Ala Gln Val Val Arg Ala Tyr Ser
            20                  25                  30

Arg Pro His Gly Leu Gln Val Arg Asp Gly Asn Pro Gly Asn Ala Ser
        35                  40                  45

Gln Thr Tyr Glu Thr Arg Phe Pro Gly Val Thr Trp Asp Gln His Asn
    50                  55                  60

Trp Arg Leu Thr Ser Thr Val Leu Asp Gln Gly His Tyr Gln Ser Arg
65                  70                  75                  80

Gly Ser Ile Ala Asn Gly Tyr Val Gly Ile Asn Val Ala Ser Ala Gly
                85                  90                  95

Pro Phe Phe Glu Leu Asp Thr Pro Val Asp Gly Asp Val Ile Asn Gly
            100                 105                 110

Trp Pro Leu Phe Ser Arg Arg Gln Thr Phe Ala Thr Ile Ala Gly Phe
        115                 120                 125

Tyr Asp Glu Gln Pro Arg Thr Asn Gly Thr Asn Phe Pro Trp Leu Tyr
    130                 135                 140

Gln Tyr Gly Gly Glu Ser Val Ile Ser Gly Val Pro His Trp Ser Gly
145                 150                 155                 160

Leu Val Leu Asp Leu Gly Asp Gly Asn Tyr Leu Asp Ala Thr Val Asp
                165                 170                 175

Ser Ser Thr Ile Ser Asp Tyr Ser Thr Val Tyr Asp Tyr Lys Ala Gly
            180                 185                 190

Ile Leu Ser Trp Ser Tyr Thr Trp Thr Pro Lys Gly Asn Lys Gly Ser
        195                 200                 205

Phe Lys Ile Asn Tyr Ser Leu Phe Ala His Lys Leu Tyr Val Asn Gln
    210                 215                 220

Ala Val Val Arg Leu Asp Ile Thr Pro Ser Thr Asn Thr Asn Ala Thr
225                 230                 235                 240

Val Val Asn Val Ile Asp Gly Tyr Ser Ala Val Arg Thr Asp Phe Val
                245                 250                 255

Gly Ser Gly Lys Asp Gly Asp Ala Ile Tyr Ser Ala Val Arg Pro Trp
            260                 265                 270

Gly Ile Ser Asn Val Thr Ala Tyr Ile Tyr Thr Val Leu Asp Gly Ser
        275                 280                 285

Asn Gly Val Asp Leu Ser Ser Ser Ala Ile Val Asn Asn Lys Pro Tyr
    290                 295                 300

Ile His Thr Asn Asp Ser Ser Ile Ala Gln Ala Val Asn Val Gly Phe
305                 310                 315                 320

Arg Ser Gly Lys Thr Val Thr Ile Thr Lys Phe Val Gly Ala Ala Ser
                325                 330                 335

Ser Asp Ala Phe Pro Asn Pro Gln Gln Thr Ala Lys Asp Ala Ala Leu
            340                 345                 350

Thr Ala Lys Lys Lys Gly Tyr Asp Ala Leu Leu His Ser His Val Ala
        355                 360                 365
```

```
Glu Trp Ala Ala Val Met Pro Asp Glu Ser Val Asp Asp Phe Thr Phe
370                 375                 380
Pro Glu Asn Gly Thr Leu Pro Gln Asp Pro Phe Ile Ile Glu Ser Ala
385                 390                 395                 400
Ile Thr Ala Val Val Asn Pro Tyr Tyr Leu Leu Gln Asn Thr Val Gly
            405                 410                 415
Glu Asn Ala Leu Lys Glu Ile Ser Asn Ala Pro Val Asn Glu Trp Ser
        420                 425                 430
Ile Ser Val Gly Gly Leu Thr Ser Asp Ser Tyr Ala Gly Leu Ile Phe
    435                 440                 445
Trp Asp Ala Asp Leu Trp Met His Pro Gly Leu Ala Ala Ala Phe Pro
450                 455                 460
Lys Ala Ala Gln Arg Ile Pro Asn Tyr Arg Val Ala Lys Tyr Gln Gln
465                 470                 475                 480
Ala Arg Arg Asn Val Lys Thr Ala Phe Thr Ser Ser Lys Asn Glu Thr
            485                 490                 495
Trp Phe Ser Asp Ser Ala Ala Val Tyr Pro Trp Thr Ser Gly Arg Tyr
        500                 505                 510
Gly Asn Cys Thr Gly Thr Gly Pro Cys Trp Asp Tyr Glu Tyr His Leu
    515                 520                 525
Asn Gly Asp Ile Gly Leu Ser Leu Ile Asn Gln Trp Val Ala Ser Gly
530                 535                 540
Asp Thr Lys Thr Phe Gln Glu Ser Tyr Phe Pro Ile Tyr Asp Ser Ile
545                 550                 555                 560
Ala Thr Leu Tyr Ala Asp Leu Leu Gln Pro Asn Gly Thr His Trp Thr
            565                 570                 575
Leu Thr Asn Met Thr Asp Pro Asp Glu Tyr Ala Asn Ala Val Asp Ala
        580                 585                 590
Gly Gly Tyr Thr Met Pro Leu Ile Ala Gln Thr Leu Leu Tyr Ala Asn
    595                 600                 605
Ser Phe Arg Lys Gln Phe Gly Ile Gln Gln Asn Asn Thr Trp Thr Asp
610                 615                 620
Met Ala Ser Asn Ile Leu Leu Leu Arg Glu Asn Asp Val Thr Leu Glu
625                 630                 635                 640
Tyr Thr Thr Met Asn Asn Ser Val Gln Val Lys Gln Ala Asp Val Val
            645                 650                 655
Leu Val Thr Tyr Pro Leu Asp Tyr Thr Ser Asn Tyr Ser Ser Thr Asp
        660                 665                 670
Ala Leu Asp Asp Leu Asp Tyr Tyr Ala Leu Lys Gln Ser Pro Asp Gly
    675                 680                 685
Pro Gly Met Thr Tyr Ala Ile Phe Ser Ile Val Ala Asn Glu Val Ser
690                 695                 700
Pro Ser Gly Cys Ser Val Tyr Thr Tyr Ala Gln Tyr Ser Tyr Asp Pro
705                 710                 715                 720
Tyr Val Arg Ala Pro Phe Phe Gln Phe Ser Glu Gln Leu Val Asp Asp
            725                 730                 735
Tyr Thr Leu Asn Gly Gly Thr His Pro Ala Tyr Pro Phe Leu Thr Gly
        740                 745                 750
His Gly Gly Ala Asn Gln Val Ile Tyr Gly Tyr Leu Gly Leu Arg
    755                 760                 765
Leu Leu Pro Asp Asp Val Ile His Ile Asp Pro Asn Leu Pro Pro Gln
770                 775                 780
Val Pro His Val Lys Tyr Arg Thr Phe Tyr Trp Arg Gly Trp Pro Ile
```

```
                                785                 790                 795                 800
        Gln Ala Ser Ser Asn Tyr Thr His Thr Thr Leu Arg Arg Ala Ala His
                        805                 810                 815
        Val Gln Ala Leu Asp Thr Ala Asp Gln Arg Phe Ala Lys Thr Ala Ile
                        820                 825                 830
        Pro Val Gln Val Gly Ser Gly Lys Asn Val Thr Val Tyr Gln Leu Pro
                        835                 840                 845
        Val Asn Gly Gln Leu Thr Val Pro Asn Arg Gln Val Gly Ser Lys Leu
                        850                 855                 860
        Thr Val Pro Gly Asn Leu Ala Gln Cys Gln Pro Val Gln Ser Gln Asp
        865                 870                 875                 880
        Ser Tyr Glu Pro Gly Gln Tyr Pro Met Ala Ala Val Asp Gly Ala Ala
                        885                 890                 895
        Ser Thr Lys Trp Gln Pro Ser Ser Ala Ala Asn Thr Ser Ser Leu Thr
                        900                 905                 910
        Val Ser Leu Pro Gln Ser Glu Ser Gly Thr Met Val Ser Gly Phe Tyr
                        915                 920                 925
        Phe Asp Trp Ala Gln Ala Pro Pro Val Asn Ala Thr Val Phe His
                        930                 935                 940
        Asn Asp Thr Ser Glu Asp Pro Leu Ser Ala Ser Ala Gly Gly Gln Tyr
        945                 950                 955                 960
        Phe Val Thr Asn Ile Asn Asn Ile Thr Leu Ser Ser Pro Tyr Asn Pro
                        965                 970                 975
        Gln Ala Asn Ser Ala Asp Ala Ile Met Leu Pro Ser Ser Asn Thr Thr
                        980                 985                 990
        Asn Val Thr Leu Ala Gln Pro Val Pro Val Pro Arg Tyr Ala Thr Leu
                        995                 1000                1005
        Tyr Ile Thr Gly Asn Gln Ala Leu Ser Glu Ser Asp Val Gln Ala
                        1010                1015                1020
        Gln Asn Gly Thr Gly Ala Thr Val Ala Glu Trp Ala Ile Leu Ala
                        1025                1030                1035
        Ser Asn Pro Gln Ala Gly Phe Pro Ser Glu Lys Ser Arg Cys Glu
                        1040                1045                1050
        Ala Ser Val Ala Arg Leu Trp Leu Asp Cys Met Leu Gly Gly
                        1055                1060                1065
```

<210> SEQ ID NO 9
<211> LENGTH: 2229
<212> TYPE: DNA
<213> ORGANISM: Artificial Sequence
<220> FEATURE:
<223> OTHER INFORMATION: Ms37

<400> SEQUENCE: 9

| | |
|---|---|
| atggcgctac gacacatcgc ggcggcggcg atcgccggtc ttgcctcaag gactgcagcg | 60 |
| ctgtacatca atggctcagt cacagcgccg tgcgactcgc ccatttactg ccaaggcgag | 120 |
| cttctaaaag cggttgaact ggcgcgtcct tcgttgaca gcaagacatt tgtggacatg | 180 |
| taagtcatga tcggccagcc aggtgggaat gcagccggcg ggcagattcg tggtgacaca | 240 |
| ctgactgact tggattcccg cccaggccca cgatcaagcc agtggatgaa gtgcttgcag | 300 |
| cattcagcaa gcttagccta ccactttcca ataactcaga gctcaacgcc ttcttgtatg | 360 |
| agaacttcgc ccaggctggc cacgagctcg aagaagtgcc cgacagtgag ctagagacgg | 420 |
| acgcaaagtt cctcgacaag ctcgaggatc gcaccatcaa ggagttcgtc ggcaaggtga | 480 |

-continued

| | |
|---|---|
| tcgacatctg gcccgacttg accaggcgct atgccggccc cagcaactgc accgagtgcg | 540 |
| ccaacagctt cattcccgtg aaccgcacgt tcgtcgtggc tggcggtcgc ttccgagagc | 600 |
| cctactattg ggattcgtac tggatcgtcg aaggtctcct gcgcactggc ggtgccttca | 660 |
| cccatatctc caagaacatc attgagaact tcctggactt tgtcgacacg attggcttca | 720 |
| ttcccaatgg cgccaggatc tactacctga acaggtcaca gcccctctc ctgacattga | 780 |
| tggtgaagag ctacgtcgac tacaccaacg acacgagcat cctggacagg gccttgccgc | 840 |
| tgctgatcaa ggagcacgag ttcttcatga ataaccggac ggtgtccatc acgggatcga | 900 |
| acggcaagga gtacactctg aacaggtaag cgaggtggac aggcaggcct cggcgaccat | 960 |
| gcgcttattg ttgtatctgg caggtatcac gttgaaaaca accaaccacg cccagagtcg | 1020 |
| ttccgggagg attacattac cgctaacaac ggctccctact acgcgtcttc gggcataata | 1080 |
| tatcccgtta agacgcccct caacgagacg gaaaaggccg cgctctactc gaacctagca | 1140 |
| accggcgccg agtccggctg ggactacacc tcccgatggc ttggggtccc cagcgacgct | 1200 |
| gcgagggacg tctatttccc gctccgctcg cttaatgtcc gcgacatagt ccccgtcgat | 1260 |
| ctcaactcca tcctctacca gaacgaggtg atcattgccg agtacctcga gaaggccggt | 1320 |
| aactcctccg cggccaagcg cttcgccact gctgccgaac agcgcagcga ggccatgtac | 1380 |
| tccctcatgt ggaacgccac gcactggtct tactttgact acaatctgac cgataacacg | 1440 |
| caacacatct tcgtcccagc cgacgaggac accgcccccc aggaccggat cgaggccccc | 1500 |
| cccggtcaac aagtcttctt ccacattgcg cagctctatc cattctggac gggcgcggcc | 1560 |
| cccgccagcc ttaaggctaa ccccctcgcg gtgcagcaag cctacgcccg tgtggcgcgc | 1620 |
| atgctcgata tcaagaaggg cgccatcccc gccaccaact accgcaccgg ccaacaatgg | 1680 |
| gaccagccca acgtctggcc gccgctgcaa catatcctga tgaagggcct gcttaacacc | 1740 |
| ccggcaacct ttggcaagtc cgaccctgcg taccagagcg tgcaaaacct cgccctgcgt | 1800 |
| ctcgcccagc gctacctcga ttccaccttt tgtacctggt acgccacggg cggttcaacc | 1860 |
| agcgacttcc cgcagctgga gggtgttacc ccgggcgcta cgggcgtcat gtttgagaag | 1920 |
| tacgccgaca tgctaccaa cgttgccggc ggcggcggcg aatacgaggt cgtcgagggt | 1980 |
| ttcgggtgga ccaatggcgt actgatctgg gcggccgacg tctttggtaa caagctcaag | 2040 |
| cgcccggact gcggcaacat cacggccgca cataccccact ctagtgccaa gagaggtctg | 2100 |
| gaagagaata agctgccgag gagggcggtg gagctcgacc cgtgggatgc cgcgtggacc | 2160 |
| aagatgtttg gcggagtaa gctccggaga agagaggcag aagatgtgcg gaagcggtgg | 2220 |
| atgagctaa | 2229 |

<210> SEQ ID NO 10
<211> LENGTH: 3454
<212> TYPE: DNA
<213> ORGANISM: Artificial Sequence
<220> FEATURE:
<223> OTHER INFORMATION: Tr65

<400> SEQUENCE: 10

| | |
|---|---|
| atgcggtcga cagtgagtgg cccatgatgt gcctcacgtt ggaaaggggg cacgtaaaca | 60 |
| cttgcaatca atgctaacat ttgaactctg ttgctctcag gtcacttctg cggcggcgct | 120 |
| gctgtcgctg cttcagcttg tttctccggt ccatggcaca acactcgttg accgcgtcac | 180 |
| caagtgtctc agcagacacg acggctcaga cgcggaatcc cacttcagca aaaacgtcta | 240 |
| caagaccgac ttcgccggcg taacgtggga cgaggacaac tggctgctca gcacgacgca | 300 |

```
gctcaagcag ggcgccttcg aggcccgcgg ctccgtggcc aatggctacc tgggcatcaa    360
cgtcgccagc gtcgggccct ttttcgaggt cgacaccgag gaggacggcg atgtcatcag    420
cggctggccc ctgttctcga ggcggcagtc gtttgcgacc gttgccggct tctgggacgc    480
gcagccgcag atgaacggga ccaacttccc gtggctctcg cagtacggct ccgacacggc    540
catcagcggc atcccgcact ggagcggcct cgtcctggac ctcggggcg gcacgtacct     600 cgatgccacg gtcagcaaca agaccatctc ccacttccgc tcgacctacg actacaaggc    660
cggcgtgctg agctggtcgt acaagtggac gcccaagggc aacaagggct cctttgacat    720
ctcgtaccgc ctctttgcca acaagctgca cgtgaaccag gccgtcgtcg acatgcaggt    780
caccgcgtcc aagaacgtgc aggcgtccat cgtcaacgtc ctcgacggct tgctgccgt     840 gcgcaccgac tttgtcgagt ccggcgagga cggcagtgcc atcttcgcgg cggtgcggcc    900
aaatggcgtc gccaacgtca cggcctacgt ctatgctgat atcaccggat ctggaggcgt    960
caacctgtcg agccgcaaga tcgtgcacaa caagccgtat gtacacgcca acgcatcgtc   1020
cattgcacag gctgtccccg tcaagttcgc cgccggacgc accgtgcggg tgaccaagtt   1080
tgtgggagcc gcctcctctg atgccttcaa gaaccccaag caggtcgcca agaaggcagc   1140
cgctgcaggc ctcagcaatg gatataccaa gtccctcaag gcgcacgtcg aggaatgggc   1200
caccgtcatg cccgagagct ccgtcgacag cttcgccgac cccaagacgg gcaagctccc   1260
tgccgacagc cacatcgtgg actctgccat cattgcagtc accaacacct actatctgct   1320
gcagaacacg gtgggcaaga atggcatcaa ggcagtcgac ggagcccgg tcaacgtgga    1380 cagcatctcc gtcggcggac tgacgtcgga ctcgtatgcc ggccagatct ctgggacgc    1440 cgacctctgg atgcagcccg gcctggtggc cgctcacccg gaggccgccg agagaatcac   1500
aaactaccgc ctcgcgcgat acggccaggc caaggagaac gtcaagacgg cctatgcggg   1560
ctcccagaac gagaccttct tctcggcctc tgcggccgtg ttcccgtgga ccagcggccg   1620
gtacggcaac tgtaccgcta ctggcccctg ctgggactac gagtaccatt tgaacggcga   1680
cattggcatt tctctggtca accagtgggg ggtgaacggt gacaccaagg actttgagaa   1740
gaatctcttc ccagtgtacg actcggttgc ccagctgtac ggcaacctgc tccggccgaa   1800
caagacgtcg tggacactga ccaacatgac cgatcctgta cgtttgattg attattcctg   1860
acacgcattg gctaacactt tgaacaggat gaatatgcaa accacgtcga cgccggtgga   1920
tacaccatgc cgctcatcgc agagacgctc caaaaggcca acagcttccg ccagcagttt   1980
ggcatcgagc agaacaagac gtggaacgac atggcgtcca acgtcctggt tcttcgcgag   2040
aacggggtga cgctcgagtt cacggccatg aacggaaccg cagtggtcaa gcaggccgat   2100
gtgattatgc tcacctaccc cctgagttac ggcaccaact acagcgcgca agatgctctc   2160
aacgacctcg actacgtgag tctgcccttt cgttcaagct gataatgagc tacctacgta   2220
tattgccatg ctaacaatct tctgcctgca gtatgccaac aagcaatcgc ccgacggacc   2280
ggccatgaca tatgccttct tctccatcgt cgccaacgaa atctctccct cgggctgctc   2340
ggcctacacg tacgcgcaaa acgccttcaa gccctacgtc cgcgcccct tctaccagat    2400 atccgagcag ctcatcgacg atgccagcgt caacggcggc acgcaccctg cctacccgtt   2460
cctcaccggc cacggcggcg cccaccaggt cgtcctcttt ggctacctcg gctccggct    2520 ggtgccagac gacgtcatcc acatcgagcc caacctgccc cctcagatcc cgtatctgag   2580
atacaggacg ttttactggc gcggctggcc catctcggcc tggtccaact acacgcacac   2640
```

```
gaccctcagc cgcgccgccg gcgttgctgc gctcgagggg gcggaccagc ggtttgctcg    2700
caagcccatc accatccacg ccggccccga acaggaccca acagcgtacc ggctgcccgt    2760
caagggctcc gtcgtgatcc ccaacaagca gatcggctct cagcagacat acgccggcaa    2820
cctggtgcag tgccacgccg ccagctctcc caacgactac gtgccgggcc agttccccat    2880
tgccgccgtc gatggcgcca cgtctaccaa gtggcagccc gcctccgccg acaaggtcag    2940
ctccatcacc gtgtcactgg acaaggagga cgtgggatct ctggtgtcgg gcttccattt    3000
cgactgggcc caggcccctc ccgtcaacgc caccgtcatc ttccacgacg aggcccttgc    3060
ggatcctgcc acggcgctcg cctccgcgca caagcacaac tccaagtaca caaccgtcac    3120
ctcgttgaca aacattgagc tgtccgaccc gtacgtttcg accaaggacc tcaacgccat    3180
tgccatcccc attggcaaca cgaccaacgt caccctctcg caccccgtgg ccgcttcccg    3240
atatgcatcc ctcctcatcg tcgggaacca gggcctcgac cccgtggacg tcaaagcaaa    3300
gaacggcacc ggcgctacgg tggcggagtg ggctatcttt ggccatggca aggagcactc    3360
tggcaagccg agctctcaca gcaagaggag gttgaatgtc cggaccgcgg ccactttgtc    3420
gaatccgagg agctttatgc gtcggcgttt gtaa                               3454
```

```
<210> SEQ ID NO 11
<211> LENGTH: 23
<212> TYPE: DNA
<213> ORGANISM: Artificial Sequence
<220> FEATURE:
<223> OTHER INFORMATION: Primer vector-F

<400> SEQUENCE: 11
cttggcgtaa tcatggtcat agc                                             23

<210> SEQ ID NO 12
<211> LENGTH: 40
<212> TYPE: DNA
<213> ORGANISM: Artificial Sequence
<220> FEATURE:
<223> OTHER INFORMATION: Primer vector-R

<400> SEQUENCE: 12
cggacccctc cgccaatggc cttgcatgca ggcctctgca                           40

<210> SEQ ID NO 13
<211> LENGTH: 20
<212> TYPE: DNA
<213> ORGANISM: Artificial Sequence
<220> FEATURE:
<223> OTHER INFORMATION: Primer amdS-F

<400> SEQUENCE: 13
ctagatctac gccaggaccg                                                 20

<210> SEQ ID NO 14
<211> LENGTH: 40
<212> TYPE: DNA
<213> ORGANISM: Artificial Sequence
<220> FEATURE:
<223> OTHER INFORMATION: Primer amdS-R

<400> SEQUENCE: 14
atgaccatga ttacgccaag cttctggaaa cgcaaccctg                           40

<210> SEQ ID NO 15
<211> LENGTH: 20
```

```
<212> TYPE: DNA
<213> ORGANISM: Artificial Sequence
<220> FEATURE:
<223> OTHER INFORMATION: Primer gla-F

<400> SEQUENCE: 15
gccattggcg gaggggtccg                                              20

<210> SEQ ID NO 16
<211> LENGTH: 40
<212> TYPE: DNA
<213> ORGANISM: Artificial Sequence
<220> FEATURE:
<223> OTHER INFORMATION: Primer gla-R

<400> SEQUENCE: 16
cggtcctggc gtagatctag atgcattgaa tgacagtgat                        40

<210> SEQ ID NO 17
<211> LENGTH: 40
<212> TYPE: DNA
<213> ORGANISM: Artificial Sequence
<220> FEATURE:
<223> OTHER INFORMATION: Primer Thi37-F

<400> SEQUENCE: 17
agcatcatta cacctcagca atggcaccgc gaagcttcgt                        40

<210> SEQ ID NO 18
<211> LENGTH: 40
<212> TYPE: DNA
<213> ORGANISM: Artificial Sequence
<220> FEATURE:
<223> OTHER INFORMATION: Primer Thi37-R

<400> SEQUENCE: 18
gtcaccctct agatctcgag tcaagcagcc aacaaccacc                        40

<210> SEQ ID NO 19
<211> LENGTH: 40
<212> TYPE: DNA
<213> ORGANISM: Artificial Sequence
<220> FEATURE:
<223> OTHER INFORMATION: Primer Myc37-F

<400> SEQUENCE: 19
agcatcatta cacctcagca atggccctcc gccacgccgc                        40

<210> SEQ ID NO 20
<211> LENGTH: 40
<212> TYPE: DNA
<213> ORGANISM: Artificial Sequence
<220> FEATURE:
<223> OTHER INFORMATION: Primer Myc37-R

<400> SEQUENCE: 20
gtcaccctct agatctcgag ttaggaggac cagcgcttgc                        40

<210> SEQ ID NO 21
<211> LENGTH: 40
<212> TYPE: DNA
<213> ORGANISM: Artificial Sequence
<220> FEATURE:
<223> OTHER INFORMATION: Primer Tem65-F

<400> SEQUENCE: 21
```

| | |
|---|---|
| agcatcatta cacctcagca atgcagtcca aggtgagtgt | 40 |

<210> SEQ ID NO 22
<211> LENGTH: 40
<212> TYPE: DNA
<213> ORGANISM: Artificial Sequence
<220> FEATURE:
<223> OTHER INFORMATION: Primer Tem65-R

<400> SEQUENCE: 22

| | |
|---|---|
| gtcaccctct agatctcgag tcacccgccg agcatgcagt | 40 |

APPLICATION OF TREHALASE IN FERMENTATIVE PRODUCTION

CROSS REFERENCE TO RELATED APPLICATIONS

This application is the U.S. National Stage of International Patent Application No. PCT/CN2019/106078, filed on Sep. 17, 2019, and published in Chinese under PCT Article 21(2) as WO2020/057476A1 on Mar. 26, 2020. PCT/CN2019/106078 claims the benefit of priority from Chinese Patent Application No. 201811083590.3, filed on Sep. 17, 2018.

BACKGROUND

Technical Field

The disclosure relates to a process for producing fermented products, and in particular relates to preparation of polypeptides with trehalase activity and application of trehalase in fermentative production.

Related Art

Trehalase ($\alpha,\alpha$-trehalase, E.C 3.2.1.28) is a glycoside hydrolase that can specifically hydrolyze trehalose containing $\alpha$-1,1 glycosidic bonds and release two molecules of glucose. Trehalase exists widely in bacteria, fungi, plants and animals. According to its optimal pH, trehalase can be divided into neutral trehalase and acid trehalase, and is located in different positions of the cell, i.e. inside the cell and outside the cell. Studies have shown that trehalase exists in the brush border membrane of the kidney and the chorion of the small intestine of mammals, and may be related to the degradation of trehalose in the cell tissue environment. In microorganisms, trehalase also plays a vital role in many physiological processes, such as fungal spore germination and resting cell growth resumption.

In the process of alcohol fermentation, yeast cells can synthesize the protective substance trehalose under the pressure environment of high osmotic pressure and high alcohol content to maintain the stability of cell osmotic pressure and help cells resist the dehydration environment caused by the high osmotic pressure and high alcohol concentration. However, trehalose cannot be utilized by yeasts, resulting in a large accumulation of trehalose. At the end of fermentation, trehalose accounts for about 60-70% of disaccharides in the total residual sugar. This part of carbon source cannot be fermented to produce ethanol, which has become a limiting factor affecting the further progress of alcohol output. Addition of trehalase can convert the trehalose in the fermentation residual sugar into glucose that can be used by cells, and further glucose is converted into ethanol, which is a very effective method to reduce residual sugar and increase alcohol production. WO2016205127 reported that application of trehalase Ms37 in fermentative production of glucose can significantly increase the glucose content. The *Trichoderma reesei* trehalase Tr65 disclosed in WO2015065978 can increase the output of ethanol fermentation.

In the process of amino acid fermentation, a large amount of trehalose will be accumulated in the metabolic process of strains in the later stage of fermentation, and have a very adverse effect on the fermentative production of amino acids. On the one hand, part of the glucose is converted into trehalose which is difficult to utilize, resulting in a reduction in the utilization rate of carbon sources. On the other hand, the accumulation of a large amount of trehalose will have many adverse effects on the subsequent extraction and crystallization of amino acids. CN107058415A discloses that addition of trehalase in the late stage of glutamic acid fermentation can not only increase the sugar acid conversion rate in glutamic acid fermentation and reduce sugar consumption, but also facilitate the isoelectric crystallization after extraction of glutamic acid.

At present, there are very few reported trehalase applied in fermentative production, and the efficiency of fermentative production is low. With the development of genome sequencing and biotechnology, trehalase with better properties needs to be further explored and applied.

SUMMARY

The disclosure provides a method for producing a fermented product. The method includes adding a polypeptide with trehalase activity to a trehalose-containing production solution to produce the fermented product, and the polypeptide is selected from one or more in the following group:
(a) a polypeptide having at least 90% sequence identity with an amino acid sequence shown in SEQ ID NO: 6, SEQ ID NO: 7, or SEQ ID NO: 8;
(b) a polypeptide encoded by a polynucleotide which hybridizes with the following under highly stringent conditions: (i) a polypeptide encoding sequence of SEQ ID NO: 3, SEQ ID NO: 4, or SEQ ID NO: 5, (ii) a cDNA sequence thereof, or (iii) a full-length complement of (i) or (ii); and
(c) a polypeptide encoded by a polynucleotide having at least 60% sequence identity with the polypeptide encoding sequence of SEQ ID NO: 3, SEQ ID NO: 4, or SEQ ID NO: 5 or the cDNA sequence thereof.

The polypeptide with trehalase activity has at least 91%, at least 92%, at least 93%, at least 94%, at least 95%, at least 96%, at least 97%, at least 98%, or at least 99% identity with the amino acid sequence shown in SEQ ID NO: 6, SEQ ID NO: 7, or SEQ ID NO: 8. In one embodiment, the amino acid sequence of the polypeptide with trehalase activity is shown in SEQ ID NO: 6, SEQ ID NO: 7, or SEQ ID NO: 8. In another embodiment, the amino acid sequence of the polypeptide with trehalase activity is shown in SEQ ID NO: 6, or SEQ ID NO: 8. In one embodiment, the amino acid sequence of the polypeptide with trehalase activity is shown in SEQ ID NO: 6. In another embodiment, the amino acid sequence of the polypeptide with trehalase activity is shown in SEQ ID NO: 7. In another embodiment, the amino acid sequence of the polypeptide with trehalase activity is shown in SEQ ID NO: 8.

In some embodiments, the polypeptide with trehalase activity is a variant of the polypeptide shown in SEQ ID NO: 6, SEQ ID NO: 7, or SEQ ID NO: 8, including one or more (for example, a plurality of) positions containing substitutions, deletions, and/or insertions, or fragments of the polypeptide.

In some embodiments, the fermentation method as described in the disclosure involves a polypeptide with trehalase activity. The polypeptide is a polynucleotide polypeptide, and the polynucleotide hybridizes with the following under highly stringent conditions: (i) a polypeptide encoding sequence of SEQ ID NO: 3, SEQ ID NO: 4, or SEQ ID NO: 5, (ii) a cDNA sequence thereof, or (iii) a full-length complement of (i) or (ii).

In other embodiments, the fermentation method as described in the disclosure involves a polypeptide with trehalase activity. The polypeptide is encoded by a polynucleotide which hybridizes with the following under very stringent conditions: (i) a polypeptide encoding sequence of SEQ ID NO: 3, SEQ ID NO: 4, or SEQ ID NO: 5, (ii) a cDNA sequence thereof, or (iii) a full-length complement of (i) or (ii).

In some embodiments, the fermentation method as described in the disclosure involves a polypeptide with trehalase activity. The polypeptide is encoded by a polynucleotide, and the polynucleotide has at least 65% sequence identity with the polypeptide encoding sequence of SEQ ID NO: 3, SEQ ID NO: 4, or SEQ ID NO: 5 or the cDNA sequence thereof. In one embodiment, the polynucleotide has at least 70%, at least 75%, at least 80%, at least 90%, at least 91%, at least 92%, at least 93%, at least 94%, at least 95%, at least 96%, at least 97%, at least 98% or at least 99% sequence identity with the polypeptide encoding sequence of SEQ ID NO: 3, SEQ ID NO: 4, or SEQ ID NO: 5 or the cDNA sequence thereof. In another embodiment, the polynucleotide sequence is the polypeptide encoding sequence of SEQ ID NO: 3, SEQ ID NO: 4, or SEQ ID NO: 5 or the cDNA sequence thereof.

In one embodiment, the fermentation method as described in the disclosure involves a polypeptide with trehalase activity. The polypeptide is encoded by a polynucleotide, and the polynucleotide has at least 60%, at least 70%, at least 75%, at least 80%, at least 90%, at least 91%, at least 92%, at least 93%, at least 94%, at least 95%, at least 96%, at least 97%, at least 98% or at least 99% sequence identity with the polypeptide encoding sequence of SEQ ID NO: 3 or the cDNA sequence thereof. In another embodiment, the fermentation method as described in the disclosure involves a polypeptide with trehalase activity. The polypeptide is encoded by a polynucleotide, and the polynucleotide is the polypeptide encoding sequence of SEQ ID NO: 3 or the cDNA sequence thereof.

In one embodiment, the fermentation method as described in the disclosure involves a polypeptide with trehalase activity. The polypeptide is encoded by a polynucleotide, and the polynucleotide has at least 60%, at least 70%, at least 75%, at least 80%, at least 90%, at least 91%, at least 92%, at least 93%, at least 94%, at least 95%, at least 96%, at least 97%, at least 98% or at least 99% sequence identity with the polypeptide encoding sequence of SEQ ID NO: 4 or the cDNA sequence thereof. In another embodiment, the disclosure involves a polypeptide with trehalase activity. The polypeptide is encoded by a polynucleotide, and the polynucleotide is the polypeptide encoding sequence of SEQ ID NO: 4 or the cDNA sequence thereof.

In one embodiment, the fermentation method as described in the disclosure involves a polypeptide with trehalase activity. The polypeptide is encoded by a polynucleotide, and the polynucleotide has at least 60%, at least 70%, at least 75%, at least 80%, at least 90%, at least 91%, at least 92%, at least 93%, at least 94%, at least 95%, at least 96%, at least 97%, at least 98% or at least 99% sequence identity with the polypeptide encoding sequence of SEQ ID NO: 5 or the cDNA sequence thereof. In another embodiment, the disclosure relates to a polypeptide with trehalase activity. The polypeptide is encoded by a polynucleotide, and the polynucleotide is the polypeptide encoding sequence of SEQ ID NO: 5 or the cDNA sequence thereof.

In some embodiments, in the fermentation method as described in the disclosure, among the polypeptides with trehalase activity involved, the polypeptide with trehalase activity with the amino acid sequence shown in SEQ ID NO: 6 is derived from *Thielavia terrestris*; the polypeptide with trehalase activity with the amino acid sequence shown in SEQ ID NO: 7 is derived from *Myceliophthora thermophila*; and the polypeptide with trehalase activity with the amino acid sequence shown in SEQ ID NO: 8 is derived from *Rasamsonia emersonii*.

In the fermentation method as described in the disclosure, the fermented product is selected from alcohols and amino acids. The alcohols are alcohol or ethanol, preferably alcohol; and the amino acids are selected from glutamic acid, lysine, threonine, valine, proline, tryptophan, isoleucine or leucine, preferably glutamic acid and lysine.

In one embodiment, the fermented product is alcohols selected from methanol, ethanol or propanol, preferably ethanol. In one embodiment, the fermented product is an alcohol.

For fermentative production of ethanol, after fermentation, the fermented slurry is distilled to extract ethanol. The ethanol obtained according to the method of the disclosure can be used as, for example, fuel ethanol, drinking ethanol, that is, a drinkable neutral alcoholic beverage, or industrial ethanol. On the other hand, alcohol is produced according to the fermentation method of the disclosure, and the alcohol includes ethanol, methanol, propanol, or water.

In one embodiment, the fermented product is amino acids, and the amino acids are selected from glutamic acid, lysine, threonine, valine, proline, tryptophan, isoleucine or leucine, preferably glutamic acid and lysine. In one embodiment, the fermented product is glutamic acid. In another embodiment, the fermented product is lysine.

In the fermentation method of the disclosure, the trehalose-containing production solution is selected from a saccharification solution of an alcohol fermentation raw material, an alcohol fermentation solution, alcohol fermentation mature mash supernatant, an amino acid fermentation solution or amino acid fermentation solution supernatant, preferably the saccharification solution of an alcohol fermentation raw material, the alcohol fermentation mature mash supernatant, and the amino acid fermentation supernatant.

In one embodiment, in the fermentation method, the trehalose-containing production solution is selected from the saccharification solution of an alcohol fermentation raw material, the alcohol fermentation solution, or the alcohol fermentation mature mash supernatant. In another embodiment, the trehalose-containing production solution is the saccharification solution of an alcohol fermentation raw material. In another embodiment, the trehalose-containing production solution is the alcohol fermentation solution. In another embodiment, the trehalose-containing production solution is the alcohol fermentation mature mash supernatant.

In one embodiment, in the fermentation method, the trehalose-containing production solution is selected from the amino acid fermentation solution or the amino acid fermentation supernatant. In another embodiment, the trehalose-containing production solution is the amino acid fermentation solution. In another embodiment, the trehalose-containing production solution is the amino acid fermentation supernatant.

On the one hand, the disclosure relates to a method for producing a fermented product, and when the fermented product is an alcohol, the steps of production and fermentation include:

(a) adding amylase to liquefy an alcohol fermentation raw material;
  optionally pre-saccharifying the liquefied material before step (b);
(b) saccharifying the liquefied raw material;
(c) adding yeast and performing fermentation;

(d) collecting alcohol mature mash after the end of fermentation;

wherein the trehalase can be present and/or added in the following steps:

the saccharification step (b);

the fermentation step (c);

the saccharification step and the fermentation step simultaneously;

the alcohol mature mash after the end of fermentation; and optionally the pre-saccharification step before the step (b).

In some embodiments, in the method for producing a fermented product, the added amount of the trehalase is 0.05-10 U/g DS, preferably 0.1-5 U/g DS, more preferably 0.2-0.5 U/g DS.

In some embodiments, the added amount of the trehalase is 0.05-10 U/g DS. In some embodiments, the added amount of the trehalase is 0.1-5 U/g DS. In some embodiments, the added amount of the trehalase is 0.2-0.5 U/g DS. In some embodiments, the added amount of the trehalase is about 0.1, about 0.2, about 0.3, about 0.4, and about 0.5 U/g DS. In one embodiment, the added amount of the trehalase is about 0.2 U/g DS. In one embodiment, the added amount of the trehalase is about 0.3 U/g DS. In one embodiment, the added amount of the trehalase is about 0.4 U/g DS. In another embodiment, the added amount of the trehalase is about 0.5 U/g DS.

In some embodiments, in the method for producing a fermented product, the fermentation step further includes adding a saccharifying enzyme in the step (b), and the saccharifying enzyme is preferably a complex saccharifying enzyme; and a nitrogen source is added in the step (c).

In one embodiment, in the method for producing a fermented product, in the step (a), the amylase is thermostable amylase with an added amount of 1-200 U/g DS; in the step (b), the saccharifying enzyme is a complex saccharifying enzyme with an added amount of 20-600 U/g DS; in the step (c), the yeast is active dry yeast with an added amount of 100-1500 ppm; and the nitrogen source is urea with an added amount of 100-1000 ppm.

In one embodiment, in the step (a), the amylase is thermostable amylase with an added amount of 1-200 U/g DS, preferably 10-100 U/g DS.

In one embodiment, in the step (b), the saccharifying enzyme is a complex saccharifying enzyme with an added amount of 20-600 U/g DS, preferably 50-500 U/g DS.

In one embodiment, in the step (c), the yeast is active dry yeast with an added amount of 100-1500 ppm, preferably 200-1000 ppm; and the nitrogen source is urea with an added amount of 100-1000 ppm, preferably 600 ppm.

In one embodiment, in the method for producing a fermented product, 10-100 U/g DS thermostable amylase is added in the step (a) to liquefy the alcohol fermentation raw material; the steps (b) and (c) are performed simultaneously, the pH of the raw material liquefied solution is adjusted to acidity, 50-500 U/g DS complex saccharifying enzyme, 200-1000 ppm active dry yeast, 600 ppm urea and 0.2-0.5 U/g DS trehalase are added, and fermentation is performed at 28° C.-36° C. for 48-96 h; and alcohol mature mash is collected in the step (d).

In another embodiment, in the method for producing a fermented product, 10-100 U/g DS thermostable amylase is added in the step (a) to liquefy the alcohol fermentation raw material; the steps (b) and (c) are performed simultaneously, the pH of the raw material liquefied solution is adjusted to acidity, 50-500 U/g DS complex saccharifying enzyme, 200-1000 ppm active dry yeast, and 600 ppm urea are added, and fermentation is performed at 28° C.-36° C. for 48-96 h; and alcohol mature mash is collected in the step (d), the supernatant is taken, and 0.2-0.5 U/g DS trehalase is added.

On the other hand, according to the method for producing a fermented product provided by the disclosure, when the fermented product is an amino acid, the steps of production and fermentation include:

(a) culturing a seed solution of amino acid fermentation strains;

(b) performing fermentation culture;

(c) collecting the fermentation solution;

wherein the trehalase can be present and/or added in the following steps:

the fermentation culture step (b); and the fermentation solution collection step (c).

In some embodiments, the added amount of the trehalase is 0.05-5 U/ml, preferably 0.1-2.0 U/ml, more preferably 0.2-1.0 U/ml, most preferably 0.5 U/ml. In one embodiment, the added amount of the trehalase is 0.05-5 U/ml. In one embodiment, the added amount of the trehalase is 0.1-2 U/ml.

In one embodiment, the trehalase is about 0.2, about 0.3, about 0.4, about 0.5, about 0.6, about 0.7, about 0.8, about 0.9, and about 1.0 U/ml. In one embodiment, the added amount of the trehalase is 0.2 U/ml. In one embodiment, the added amount of the trehalase is 0.3 U/ml. In one embodiment, the added amount of the trehalase is 0.4 U/ml. In one embodiment, the added amount of the trehalase is 0.5 U/ml. In one embodiment, the added amount of the trehalase is 0.6 U/ml. In one embodiment, the added amount of the trehalase is 0.7 U/ml. In one embodiment, the added amount of the trehalase is 0.8 U/ml.

In one embodiment, when the fermented product is an amino acid, in the step (a), a seed culture solution is obtained by shake flask culture of amino acid fermentation strains; in the step (b), an amino acid fermentation formula is prepared, a fermentation medium is sterilized, inoculation is performed with the seed culture solution, and fermentation culture is performed for 24-72 h; and the fermentation solution is obtained in the step (c).

In some embodiments, in the step (b), trehalase with an amount of 0.1-2.0 U/ml is added at the start of fermentation or in the fermentation process, more preferably 0.2-1.0 U/ml, most preferably 0.5 U/ml.

In some embodiments, trehalase with an amount of 0.1-2.0 U/ml is added to the supernatant of the fermentation solution obtained in the step (c), more preferably 0.2-1.0 U/ml, most preferably 0.5 U/ml.

In any one of the above-mentioned production fermentation methods in which the fermented product is amino acids, the amino acids are selected from glutamic acid, lysine, threonine, valine, proline, tryptophan, isoleucine or leucine, preferably glutamic acid and lysine.

The disclosure provides a method for producing a fermented product, the fermented product is an amino acid, and the production steps include: after the end of amino acid fermentation, the above-mentioned trehalase with an amount of 0.3-1 U/ml is added to the fermentation supernatant for performing reaction at a pH of 6.0-9.0 and a temperature of 32° C.-39° C. for 2-7 h.

The disclosure provides a method for producing a fermented product, the fermented product is glutamic acid or lysine, and the production steps include: after the end of fermentation of the glutamic acid or lysine, trehalase with an amount of 0.5 U/ml is added to the fermentation supernatant for performing reaction at a pH of 6.5-8.5 and a temperature of 32° C.-37° C. for 5 h.

The disclosure provides a method for producing a fermented alcohol. The fermentation steps include:
(a) adding amylase to liquefy an alcohol fermentation raw material;
optionally pre-saccharifying the liquefied material before step (b);
(b) saccharifying the liquefied raw material;
(c) adding yeast and performing fermentation;
(d) collecting alcohol mature mash after the end of fermentation;
wherein the method includes: trehalase is present and/or added in the following steps:
the saccharification step (b);
the fermentation step (c);
the saccharification step and the fermentation step simultaneously;
the alcohol mature mash collection step (d) after the end of fermentation; and
optionally the pre-saccharification step before the step (b),
wherein the trehalase has at least 90% sequence identity with the amino acid sequence shown in SEQ ID NO: 6, SEQ ID NO: 7, or SEQ ID NO: 8.

In some embodiments, in the above method for producing a fermented alcohol, the trehalase has at least 91%, at least 92%, at least 93%, at least 94%, at least 95%, at least 96%, at least 97%, at least 98%, or at least 99% sequence identity with the amino acid sequence shown in SEQ ID NO: 6, SEQ ID NO: 7, or SEQ ID NO: 8. In one embodiment, the trehalase has at least 90% sequence identity with the amino acid sequence shown in SEQ ID NO: 6, SEQ ID NO: 7, or SEQ ID NO: 8. In another embodiment, the trehalase has at least 91% sequence identity with the amino acid sequence shown in SEQ ID NO: 6, SEQ ID NO: 7, or SEQ ID NO: 8. In one embodiment, the trehalase has at least 92% sequence identity with the amino acid sequence shown in SEQ ID NO: 6, SEQ ID NO: 7, or SEQ ID NO: 8. In one embodiment, the trehalase has at least 93% sequence identity with the amino acid sequence shown in SEQ ID NO: 6, SEQ ID NO: 7, or SEQ ID NO: 8. In one embodiment, the trehalase has at least 94% sequence identity with the amino acid sequence shown in SEQ ID NO: 6, SEQ ID NO: 7, or SEQ ID NO: 8. In one embodiment, the trehalase has at least 95% sequence identity with the amino acid sequence shown in SEQ ID NO: 6, SEQ ID NO: 7, or SEQ ID NO: 8. In one embodiment, the trehalase has at least 96% sequence identity with the amino acid sequence shown in SEQ ID NO: 6, SEQ ID NO: 7, or SEQ ID NO: 8. In one embodiment, the trehalase has at least 97% sequence identity with the amino acid sequence shown in SEQ ID NO: 6, SEQ ID NO: 7, or SEQ ID NO: 8. In one embodiment, the trehalase has at least 98% sequence identity with the amino acid sequence shown in SEQ ID NO: 6, SEQ ID NO: 7, or SEQ ID NO: 8. In one embodiment, the trehalase has at least 99% sequence identity with the amino acid sequence shown in SEQ ID NO: 6, SEQ ID NO: 7, or SEQ ID NO: 8.

In the above method for producing a fermented alcohol, the trehalase has the amino acid sequence shown in SEQ ID NO: 6, SEQ ID NO: 7, or SEQ ID NO: 8.

In some embodiments, in the method for producing a fermented alcohol, the step (b) includes adding a saccharification enzyme, and the saccharifying enzyme is preferably a complex saccharifying enzyme; and the step (c) includes adding nitrogen.

In one embodiment, in the method for producing a fermented alcohol, the amylase in the step (a) is thermostable amylase with an added amount of 1-200 U/g DS; in the step (b), the saccharifying enzyme is a complex saccharifying enzyme with an added amount of 20-600 U/g DS; in the step (c), the yeast is active dry yeast with an added amount of 100-1500 ppm; and the nitrogen source is urea with an added amount of 100-1000 ppm.

In one embodiment, in the method for producing fermented alcohol, 10-100 U/g DS thermostable amylase is added in the step (a) to liquefy the alcohol fermentation raw material; the steps (b) and (c) are performed simultaneously, the pH of the raw material liquefied solution is adjusted to acidity, 50-500 U/g DS complex saccharifying enzyme, 200-1,000 ppm active dry yeast, 600 ppm urea and 0.2-0.5 U/g DS trehalase are added, and fermentation is performed at 28° C.-36° C. for 48-96 h; and alcohol mature mash is collected in the step (d).

In one embodiment, in the method for producing a fermented alcohol, 10-100 U/g DS thermostable amylase is added in the step (a) to liquefy the alcohol fermentation raw material; the steps (b) and (c) are performed simultaneously, the pH of the raw material liquefied solution is adjusted to acidity, 50-500 U/g DS complex saccharifying enzyme, 200-1,000 ppm active dry yeast, and 600 ppm urea are added, and fermentation is performed at 28° C.-36° C. for 48-96 h; and alcohol mature mash is collected in the step (d), and then 0.2-0.5 U/g DS trehalase is added.

A preparation method of trehalase:
A DNA construct containing a nucleic acid of codase can be constructed in a host cell for expression. Because of the well-known degeneracy in genetic encoding, different polynucleotides encoding the same amino acid sequence can be designed and prepared using conventional skills. Optimization of codons for specific host cells is also well known in the art. The nucleic acid of the codase can be incorporated into a vector.

Construction of a trehalase expression plasmid: A plasmid vector is selected, and example plasmids are pUC19 and pUC57. The nucleic acid of the codase can be operably linked to a suitable promoter to allow transcription in the host cell, and the expression vector may also contain a suitable transcription terminator. The vector may also include a selected marker, for example, a gene of which the product complements the defect in an isolated host cell, and the vector may include *Aspergillus* selected markers such as amdS and argB. The vector may also include a DNA sequence that allows the vector to replicate in the host cell. An example of such a sequence is the origin of replication of the plasmid pUC19, pUC57 or pUB110.

In one embodiment, the construction of a trehalase expression plasmid includes the following parts:
(1) a linearized vector fragment obtained by performing PCR with a pUC57 plasmid through vector-F and vector-R primers;
(2) a selected marker amdS expression cassette;
(3) DNA fragments containing the promoter and the terminator of an *Aspergillus niger* saccharifying enzyme gene;
(4) a trehalase expression cassette, wherein the trehalase genes are derived from 3 fungi respectively: the sequence of the trehalase gene derived from *Thielavia terrestris* after codon optimization is Thi37 (the nucleotide sequence is SEQ ID NO: 3, and the amino acid sequence is SEQ ID NO: 6); the sequence of the trehalase gene derived from *Myceliophthora thermophila* after codon optimization is Myc37 (the nucleotide sequence is SEQ ID NO: 4, and the amino acid sequence is SEQ ID NO: 7); and the sequence of the trehalase gene derived from *Rasamsonia emersonii* after codon optimization is Tem65 (the nucleotide sequence is SEQ ID NO: 5, and the amino acid sequence is SEQ ID NO: 8).

First, primers amdS-F and amdS-R, gla-F and gla-R are used respectively to amplify an amdS gene with a recombination arm and a DNA fragment containing gla promoter and terminator by PCR. The above linearized pUC57 vector, amdS gene and DNA fragment of gla promoter and terminator are recombined by Gibson Master Mix Kit (E2611, New England Biolabs) to obtain a pGla-amdS plasmid. The plasmid can be used for the insertion of a trehalase gene after linearization at an AflII site.

A trehalase expression vector Thi37 is constructed as follows: Primers Thi37-F and Thi37-R are used to amplify a Thi37 gene with a recombination arm by PCR, and then the Thi37 gene is recombined with the linearized pGla-amdS plasmid by Gibson Master Mix Kit (E2611, New England Biolabs) to obtain a pThi37-amdS plasmid.

A trehalase expression vector Myc37 is constructed as follows: Primers Myc37-F and Myc37-R are used to amplify a Myc37 gene with a recombination arm by PCR, and then the Myc37 gene is recombined with the linearized pGla-amdS plasmid by Gibson Master Mix Kit (E2611, New England Biolabs) to obtain a pMyc37-amdS plasmid.

A trehalase expression vector Tem65 is constructed as follows: Primers Tem65-F and Tem65-R are used to amplify a Tem65 gene with a recombination arm by PCR, and then the Tem65 gene is recombined with the linearized pGla-amdS plasmid by Gibson Master Mix Kit (E2611, New England Biolabs) to obtain a pTem65-amdS plasmid.

Transformation and integration of the trehalase expression cassettes: Three trehalase expression cassettes are introduced into *Aspergillus niger* CICC2462 strains using a protoplast transformation method, including the following steps: (1) preparation of protoplasts conventional in the art; and (2) transformation of the protoplasts, wherein the DNA fragments containing the trehalase expression cassettes obtained by ApaI linearization are used for performing mixed transformation, and positive transformants are selected from an acetamide medium.

Three types of trehalase expression cassettes Thi37-amdS, Myc37-amdS and Tem65-amdS are transformed into *Aspergillus niger* strains respectively to obtain three trehalase-positive transformants.

Expression of trehalase: A trehalase fermentation solution is obtained by culturing the recombinant trehalase *Aspergillus niger* expression strains by shake flask fermentation. Trehalase can be obtained by conventional purification methods.

Explanation of Terms

A polypeptide with trehalase activity or trehalase refers to those capable of specifically hydrolyzing trehalose containing α-1,1 glycosidic bonds and releasing two molecules of glucose. In the disclosure, the trehalase is derived from *Thielavia terrestris* trehalase, *Myceliophthora thermophila* trehalase and *Rasamsonia emersonii* trehalase. In one example, the polypeptide with trehalase activity is a polypeptide having at least 80%, at least 85%, at least 90%, at least 91%, at least 92%, at least 93%, at least 94%, at least 95%, at least 96%, at least 97%, at least 98%, at least 99% or 100% sequence identity with the amino acid sequence shown in SEQ ID NO: 6, and the polypeptide is derived from *Thielavia terrestris* and has trehalase activity. In one example, the polypeptide with trehalase activity is a polypeptide having at least 80%, at least 85%, at least 90%, at least 91%, at least 92%, at least 93%, at least 94%, at least 95%, at least 96%, at least 97%, at least 98%, at least 99% or 100% sequence identity with the amino acid sequence shown in SEQ ID NO: 7, and the polypeptide is derived from *Myceliophthora thermophila* and has trehalase activity. In one example, the polypeptide with trehalase activity is a polypeptide having at least 80%, at least 85%, at least 90%, at least 91%, at least 92%, at least 93%, at least 94%, at least 95%, at least 96%, at least 97%, at least 98%, at least 99% or 100% sequence identity with the amino acid sequence shown in SEQ ID NO: 8, and the polypeptide is derived from *Rasamsonia emersonii* and has trehalase activity.

The term "amino acid sequence" is synonymous with the terms "polypeptide", "protein" and "peptide" and can be used interchangeably. When such amino acid sequences exhibit activity, they are called "enzymes". The conventional one-letter code or three-letter code for amino acid residues is used, wherein the amino acid sequence is presented in a standard amino to carboxy terminal orientation (i.e., N→C).

The term "sequence identity" means that the correlation between two amino acid sequences or between two nucleotide sequences is described by the parameter "sequence identity". When the CLUSTALW algorithm is used for alignment with a preset parameter, the specific sequence has at least a certain percentage of amino acid residues identical to the amino acid residues of a designated reference sequence. Refer to Thompson et al. (1994) Nucleic Acids Res. 22:4673-4680. The preset parameter of the CLUSTALW algorithm is: the deletion count is the residue that is different from the reference sequence, including deletions that occur at any terminal. For example, a variant 500 amino acid residue polypeptide lacking five amino acid residues at the C-terminus has a sequence identity percentage of 99% (495/500 identical residues×100) relative to the parent polypeptide. Such variants are covered by the statement "having at least 99% sequence identity".

The term "highly stringent conditions" means that for probes of at least 100 nucleotides in length, a standard Southern blot procedure is followed, and pre-hybridization and hybridization are performed in 5×SSPE, 0.3% SDS, 200 µg/ml sheared and denatured salmon sperm DNA and 50% formamide at 42° C. for 12-24 hours. A vector material is finally washed with 2×SSC and 0.2% SDS at 65° C. three times for 15 minutes each.

The term "very highly stringent conditions" means that for probes of at least 100 nucleotides in length, a standard Southern blot procedure is followed, and pre-hybridization and hybridization are performed in 5×SSPE, 0.3% SDS, 200 µg/ml sheared and denatured salmon sperm DNA and 50% formamide at 42° C. for 12-24 hours. A vector material is finally washed with 2×SSC and 0.2% SDS at 70° C. three times for 15 minutes each.

The term "cDNA" means a DNA molecule that can be prepared by reverse transcription from a mature spliced mRNA molecule obtained from a eukaryotic or prokaryotic cell. cDNA lacks an intron sequence that may be present in the corresponding genomic DNA. The initial primary RNA transcript is the precursor of the mRNA, which is processed through a series of steps including splicing, and then appears as a mature spliced mRNA.

The term "alcohol fermentation raw material" refers to the selection of a starting material based on the desired fermented product (alcohol, i.e. ethanol). Examples of starch-containing starting materials suitable for the method of the disclosure include cereals, tubers or grains. Specifically, the starch-containing material may be corn, wheat, barley, rye, sorghum, sago, cassava, tapioca, sorghum, oats, rice, peas, beans, or sweet potatoes, or a mixture thereof, and also covers corn and barley of waxy and non-waxy types. In one embodiment, the alcohol fermentation raw material is corn. In another embodiment, the alcohol fermentation raw material is wheat.

The term "liquefied solution" refers to a starch raw material that has been liquefied. The term "saccharified solution of alcohol fermentation raw material" refers to a slurry obtained by saccharification of the liquefied solution of an alcohol fermentation raw material. The term "slurry" refers to an aqueous mixture containing insoluble solids.

The term "alcohol fermentation solution" refers to an aqueous slurry of a fermentation raw material in which microbial organisms such as ethanol-producing microorganisms and at least one enzyme such as amylase exist in the production process of alcohol.

The term "alcohol mature mash" means that the raw materials in alcohol fermentation are fermented by adding ethanol microorganisms, etc., and the fermentation mash after the end of fermentation is the alcohol mature mash.

The term "alcohol fermentation mature mash supernatant" means that the raw materials in alcohol fermentation are fermented by adding ethanol microorganisms, etc., the fermentation mash after the end of fermentation is the alcohol mature mash, and the supernatant is obtained from the alcohol mature mash by performing standing, centrifuging and other methods.

The term "amylase" or "amylolytic enzyme" refers to an enzyme that is particularly capable of catalyzing and degrading starch, including but not limited to α-amylase, β-amylase, α-glucosidase (EC 3.2.1.20; α-D-glucoside glucohydrolase), glucoamylase (EC 3.2.1.3; α-D-(1→4)-glucan glucanohydrolase), and specific product amylases such as maltotetraosidases (EC 3.2.1.60) and maltohexaosidase. Thermostable amylase refers to an amylase that remains active when exposed to higher temperatures, and usually refers to the enzyme that has thermostability or is thermostable.

The term "amino acid fermentation strains" refers to fermentative production strains commonly used in fermentative production of amino acids, usually including *Bacillus* strains. For example, glutamic acid fermentation strains include but are not limited to *Corynebacterium glutamicum, Brevibacterium tianjinese, Corynebacterium crenatum, Corynebacterium pakinense* and mutant strains thereof; lysine fermentation strains include but are not limited to *Corynebacterium glutamicum, Brevibacterium flavum, Corynebacterium crenatum,* and *Escherichia coli*; threonine fermentation strains include but are not limited to *Corynebacterium glutamicum, B. lactofermentum,* and *Escherichia coli*; proline fermentation strains include but are not limited to *Escherichia coli, Bacillus subtilis,* and *Corynebacterium glutamicum*; valine fermentation strains include but are not limited to *Brevibacterium flavum, Corynebacterium glutamicum,* and *Brevibacterium lactofermentus*; tryptophan fermentation strains include but are not limited to *Escherichia coli* and *Corynebacterium glutamicum*; isoleucine fermentation strains include but are not limited to *B. lactofermentum, Brevibacterium flavum,* and *Corynebacterium glutamicum*; and leucine fermentation strains include but are not limited to *B. lactofermentum, Brevibacterium flavum,* and *Corynebacterium glutamicum*.

The term "amino acid fermentation solution" refers to that an amino acid fermentation medium is inoculated with amino acid fermentation strains for fermentation culture to produce and accumulate specific amino acids, and in this process, the fermentation solution containing the culture medium, bacteria and fermented products is the amino acid fermentation solution.

The term "amino acid fermentation solution supernatant" refers to the supernatant obtained by performing centrifugation or membrane treatment on the fermentation solution after the end of amino acid fermentation to remove bacteria and insoluble substances.

The term "complex saccharifying enzyme": A complex enzyme refers to a combination of two or more enzymes. In the catalysis process, one enzyme uses a raw material as the substrate, and the other uses the product of the first enzyme as the substrate. Several enzymes catalyze a series of reactions together to obtain the desired product. The complex saccharifying enzyme refers to a complex high-efficiency saccharifying enzyme which is an enzyme preparation made by mixing amyloglucosidase and pullulanase in a certain ratio. Pullulanase has an action of debranching chains, and amyloglucosidase hydrolyzes liquefied starch to obtain glucose. The complex saccharifying enzyme in the disclosure is a high-efficiency complex saccharifying enzyme made by compounding a high-activity saccharifying enzyme and a pullulanase with wide pH adaptability and heat stability in an appropriate ratio, wherein the pullulanase is produced by fermentation of *Bacillus subtilis* and can quickly hydrolyze α-D-1,6 glucoside bonds in starch to produce linear dextrin; and the saccharifying enzyme is produced by fermentation of *Aspergillus niger*, can quickly hydrolyze α-D-1,4 glycosidic bonds in liquefied starch, and can also slowly hydrolyze α-D-1,6 glycosidic bonds to produce glucose. For example, Bestzyme HighDEX ultra or Bestzyme HighDEX SP high-efficiency complex saccharifying enzyme.

The term "specific activity" refers to the number of moles of a substrate that can be converted into a product by an enzyme or an enzyme preparation per unit time under specific conditions. The specific activity is generally expressed in unit (U)/mg protein.

The term "dry solids content (DS)" refers to the total solids of the slurry as a percentage of dry weight.

The phrase "simultaneous saccharification and fermentation (SSF)" refers to a process of producing biochemicals in which microbial organisms such as ethanol producing microorganisms and at least one enzyme such as amylase are present in the same treatment step. SSF includes simultaneous hydrolysis of starch substrates (granular, liquefied or solubilized) into sugars including glucose, and fermentation of the sugars into alcohols or other biochemicals or biological materials in the same reactor vessel.

The term "about" refers to ±10% of the reference value.

DETAILED DESCRIPTION

Example 1 Construction of 3 Trehalase Expression Plasmids, all of which Contain the Following Parts (1) linearization of a pUC57 plasmid through vector-F and vector-R primers;

(2) a selected marker amdS expression cassette, synthesized by GenScript company, and having a sequence shown in SEQ ID NO: 1;
(3) DNA fragments containing the gla promoter and terminator of an *Aspergillus niger* saccharifying enzyme gene, synthesized by GenScript company, and having a sequence shown in SEQ ID NO: 2;
(4) a trehalase expression cassette, wherein the trehalase genes are derived from 3 fungi respectively: the sequence of the trehalase gene derived from *Thielavia terrestris* after codon optimization is Thi37 (the nucleotide sequence is SEQ ID NO: 3, and the amino acid sequence is SEQ ID NO: 6); the sequence of the trehalase gene derived from *Myceliophthora thermophila* after codon optimization is Myc37 (the nucleotide sequence is SEQ ID NO: 4, and the amino acid sequence is SEQ ID NO: 7); and the sequence of the trehalase gene derived from *Rasamsonia emersonii* after codon optimization is Tem65 (the nucleotide sequence is SEQ ID NO: 5, and the amino acid sequence is SEQ ID NO: 8).

First, primers amdS-F and amdS-R, gla-F and gla-R were used respectively to amplify an amdS gene with a recombination arm and a DNA fragment containing gla promoter and terminator by PCR. The above linearized pUC57 vector, amdS gene and DNA fragment of gla promoter and terminator were recombined by Gibson Master Mix Kit (E2611, New England Biolabs) to obtain a pGla-amdS plasmid, and the sequence was confirmed correct by sequencing. The plasmid can be used for the insertion of a trehalase gene after linearization at an AflII site.

Figure 1A:
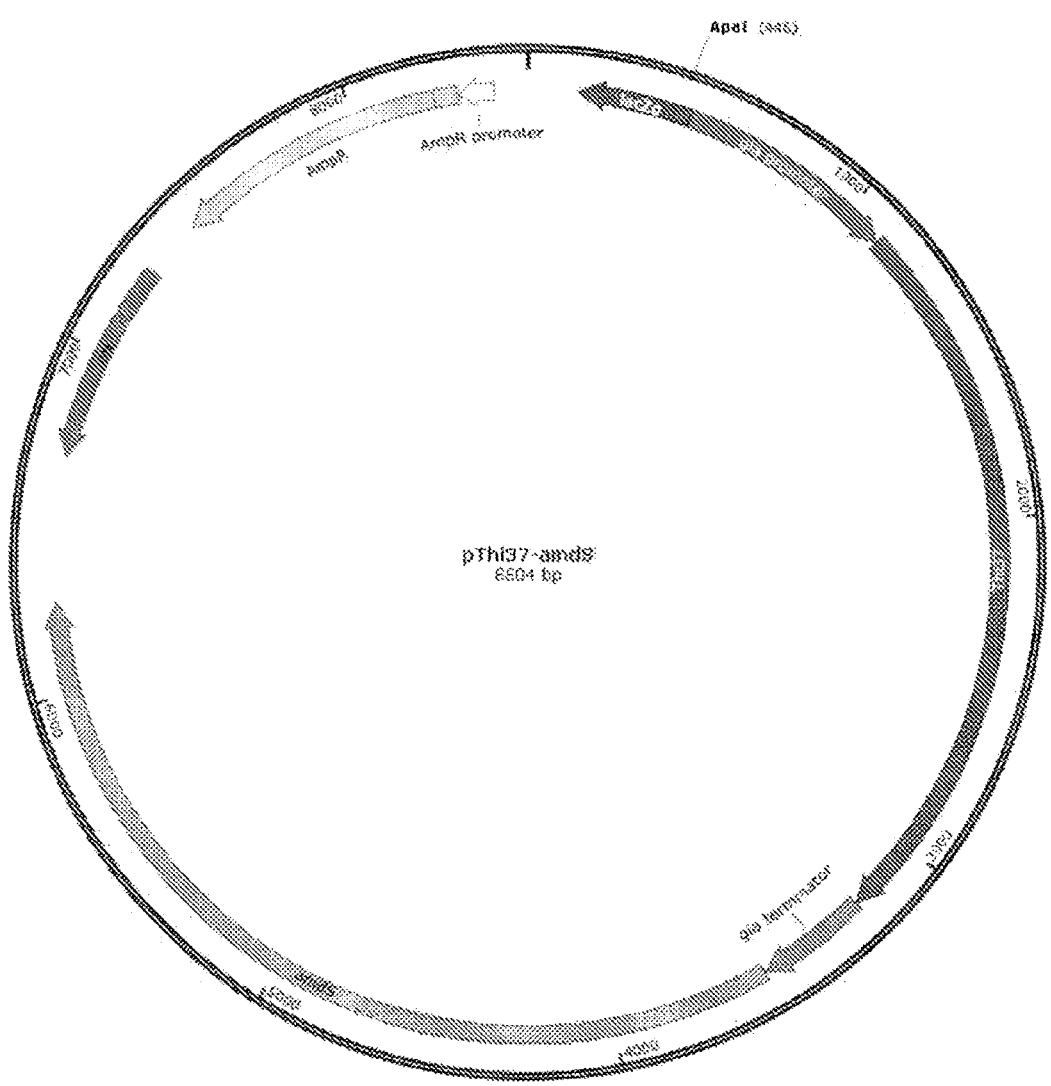
FIG. 1A Profile of the pThi37-amds plasmid.

A trehalase expression vector Thi37 was constructed as follows: Primers Thi37-F and Thi37-R were used to amplify a Thi37 gene with a recombination arm by PCR, and then the Thi37 gene was recombined with the linearized pGla-amdS plasmid by Gibson Master Mix Kit (E2611, New England Biolabs) to obtain a pThi37-amdS plasmid. The sequence was confirmed by sequencing. The profile of the constructed plasmid is shown in FIG. 1A. The plasmid can be used for protoplast transformation after linearization at the ApaI site.

Figure 1B:
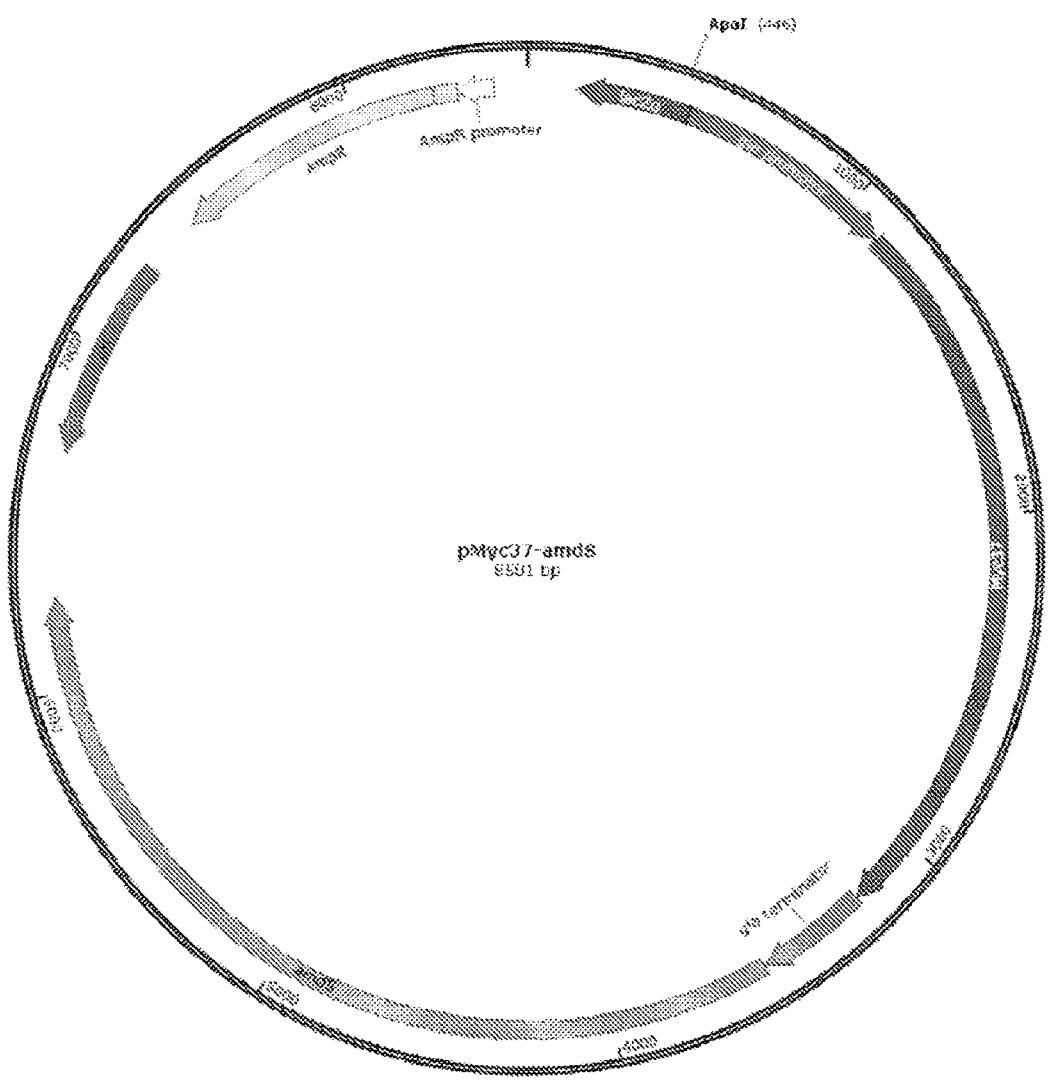
FIG. 1B Profile of the pMyc37-amds plasmid.

A trehalase expression vector Myc37 was constructed as follows: Primers Myc37-F and Myc37-R were used to amplify a Myc37 gene with a recombination arm by PCR, and then the Myc37 gene was recombined with the linearized pGla-amdS plasmid by Gibson Master Mix Kit (E2611, New England Biolabs) to obtain a pMyc37-amdS plasmid. The sequence was confirmed by sequencing. The profile of the constructed plasmid is shown in FIG. 1B. The plasmid can be used for protoplast transformation after linearization at the ApaI site.

Figure 1C:
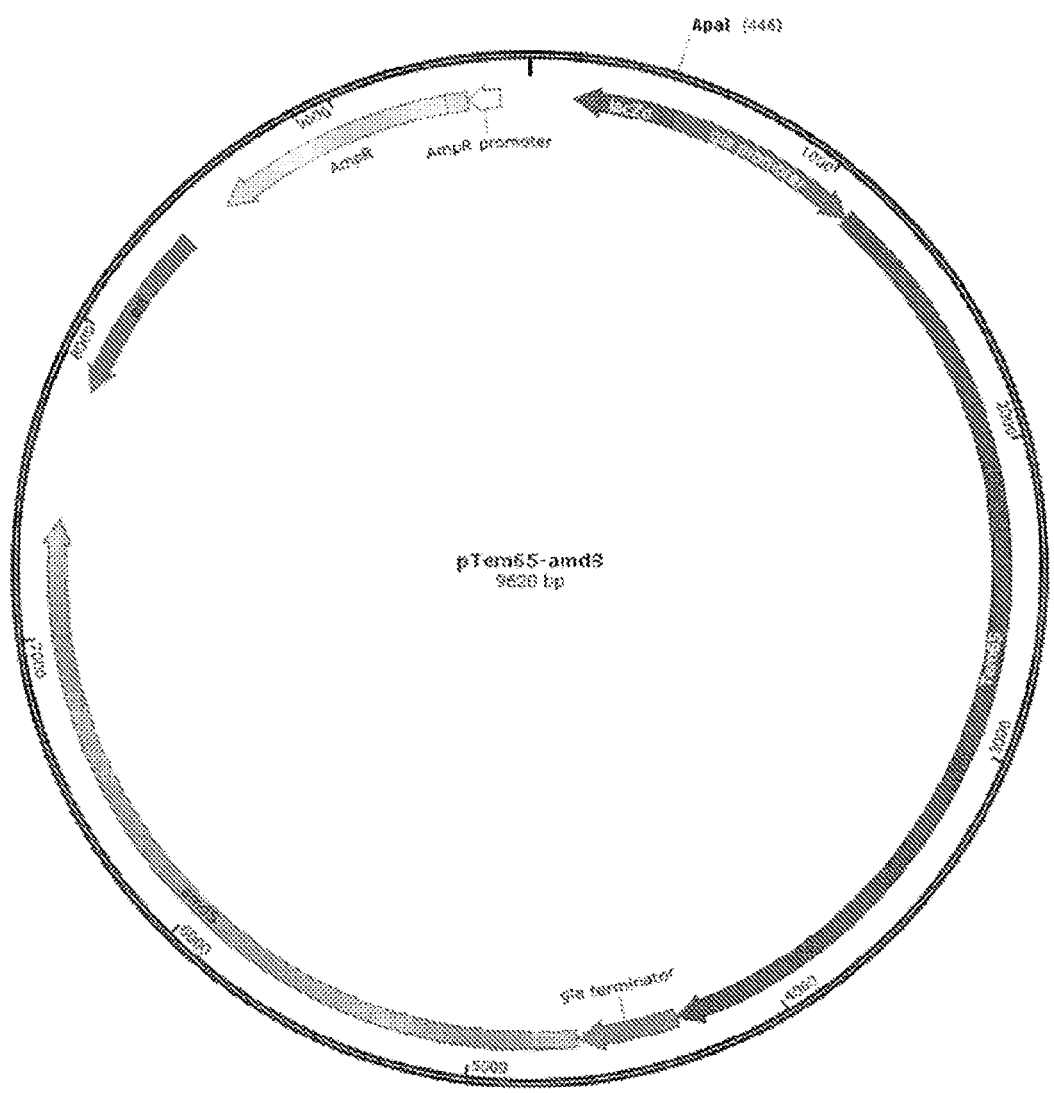
FIG. 1C Profile of the pTem65-amds plasmid.

A trehalase expression vector Tem65 was constructed as follows: Primers Tem65-F and Tem65-R were used to amplify a Tem65 gene with a recombination arm by PCR, and then the Tem65 gene was recombined with the linearized pGla-amdS plasmid by Gibson Master Mix Kit (E2611, New England Biolabs) to obtain a pTem65-amdS plasmid. The sequence was confirmed by sequencing. The profile of the constructed plasmid is shown in FIG. 1C. The plasmid can be used for protoplast transformation after linearization at the ApaI site.

The relevant primer sequences are as follows:

TABLE 1

Primers in the disclosure

| Primer name | Sequence (5'-3') |
| --- | --- |
| vector-F | CTTGGCGTAATCATGGTCATAGC (SEQ ID NO: 11) |
| vector-R | CGGACCCCTCCGCCAATGGCCTT GCATGCAGGCCTCTGCA (SEQ ID NO: 12) |
| amdS-F | CTAGATCTACGCCAGGACCG (SEQ ID NO: 13) |
| amdS-R | ATGACCATGATTACGCCAAGCTT CTGGAAACGCAACCCTG (SEQ ID NO: 14) |
| gla-F | GCCATTGGCGGAGGGGTCCG (SEQ ID NO: 15) |
| gla-R | CGGTCCTGGCGTAGATCTAGATG CATTGAATGACAGTGAT (SEQ ID NO: 16) |
| Thi37-F | AGCATCATTACACCTCAGCAATG GCACCGCGAAGCTTCGT (SEQ ID NO: 17) |
| Thi37-R | GTCACCCTCTAGATCTCGAGTCA AGCAGCCAACAACCACC (SEQ ID NO: 18) |
| Myc37-F | AGCATCATTACACCTCAGCAATG GCCCTCCGCCACGCCGC (SEQ ID NO: 19) |
| Myc37-R | GTCACCCTCTAGATCTCGAGTTA GGAGGACCAGCGCTTGC (SEQ ID NO: 20) |
| Tem65-F | AGCATCATTACACCTCAGCAATG CAGTCCAAGGTGAGTGT (SEQ ID NO: 21) |
| Tem65-R | GTCACCCTCTAGATCTCGAGTCA CCCGCCGAGCATGCAGT (SEQ ID NO: 22) |

Example 2 Transformation and Integration of Trehalase Expression Cassettes

Three trehalase expression cassettes were respectively introduced into *Aspergillus niger* CICC2462 strains (purchased from China Center of Industrial Culture Collection (CICC)) using a protoplast transformation method, including the following concrete operation steps:
(1) Preparation of protoplast: A nutrient-rich TZ liquid medium (containing 0.8% beef extract powder, 0.2% yeast extract, 0.5% peptone, 0.2% NaCl, and 3% sucrose, pH 5.8) was inoculated with *Aspergillus niger* mycelia. After culturing for 48 h, the mycelia were filtered and collected using Mira-cloth (Calbiochem company) and washed with 0.7 M NaCl (pH 5.8). After being drained, the mycelia were transferred to an enzymatic hydrolysis solution (pH 5.8) containing 1% cellulase (Sigma), 1% helicase (Sigma) and 0.2% lywallzyme (Sigma), and subjected to enzymatic hydrolysis at 30° C. and 65 rpm for 3 h. Then the enzymatic hydrolysate containing protoplasts was placed on ice and filtered with four layers of lens wiping paper. The obtained filtrate was gently centrifuged at 3,000 rpm and 4° C. for 10 min, and the supernatant was discarded. The protoplasts attached to the tube wall were washed once with an STC solution (containing 1 M D-Sorbitol, 50 mM $CaCl_2$), and 10 mM Tris, pH 7.5), and finally the protoplasts were resuspended in an appropriate amount of STC solution.

(2) Transformation of protoplasts: 10 µl (concentration: 1000 ng/µl) of DNA fragment containing a trehalase expression cassette linearized with ApaI was added to 100 µl of protoplast suspension, mixed uniformly, and stood at room temperature for 25 min. Then, a total of 900 µl of PEG solution was added in 3 times, mixed uniformly, and stood at room temperature for 25 min. Then the reaction solution was centrifuged at room temperature and 3000 rpm for 10 min, and the supernatant was discarded. The protoplasts attached to the tube wall were resuspended in 1 ml of STC solution, the STC solution was mixed with an acetamide medium (containing sucrose 3%, KCl 0.05%, $K_2HPO_4·3H_2O$ 0.1%, $FeSO_4$ 0.001%, $MgSO_4$ 0.0244%, acetamide 0.06%, and CsCl 0.34%) pre-cooled to about 45° C., and the mixed solution was spread on a plate. After the plate solidified, the plate was placed in a 34° C. incubator for 4-5 days. Transformants were picked into a new acetamide medium plate and placed in a 34° C. incubator for culturing for another 4-5 days. The transformants that grow are called positive transformants.

Using the above protoplast transformation method, the three trehalase expression cassettes Thi37-amdS, Myc37-amdS and Tem65-amdS were respectively transformed into *Aspergillus niger* strains to obtain three trehalase-positive transformants.

Example 3 Shake Flask Culture of *Aspergillus niger* Recombinant Expression Strains of Trehalase 50 ml of YPM medium (containing yeast extract 0.2%, peptone 0.2%, and maltose 2%) in shake flasks was respectively inoculated with the three trehalase-positive transformants, and cultured on a shaker at 34° C. and 220 rpm for 6 days. The supernatant of the fermentation solution was collected by centrifugation, and the trehalase activity was measured.

Example 4 Measurement of Trehalase Activity

In an enzymatic reaction system, trehalase can hydrolyze 1 molecule of trehalose into 2 molecules of glucose. The glucose produced is a reducing sugar, and can be determined by the DNS color-developing method. Definition of trehalase activity: Under the conditions of pH 4.0 and temperature 37° C., the amount of enzyme required to produce 1 µmol of glucose per minute is an enzyme activity unit.

Enzyme activity measuring method: An acetic acid-sodium acetate buffer (pH 4.0, 0.05 M) was used to dilute the enzyme solution appropriately, and 1.0 ml of the diluted solution was taken in a test tube. 1.0 ml of 1% trehalose dissolved in the acetic acid-sodium acetate buffer (pH 4.0, 0.05 M) was added, and the test tube was immediately placed in a 37° C. water bath for heat preservation. The test tube was taken out immediately after accurate reaction for 30 min. 2.5 ml of DNS color developing solution (Miller 1959) was added, the solution was boiled for 10 min, and 8 ml of distilled water was added and mixed uniformly after cooling. A spectrophotometer was used to measure the absorbance of the sample at a wavelength of 540 nm.

After activity screening by shake flasks, a trehalase THI37 high expression strain ANTHI37, a trehalase MYC37 high expression strain ANMYC37 and a trehalase TEM65 high expression strain ANTEM65 were obtained.

The supernatant of the shake flask culture fermentation solution of the trehalase THI37 high expression strain ANTHI37 was taken and subjected to protein electrophoresis (SDS-PAGE). It was observed that the molecular weight of trehalase THI37 was about 85 kDa, and the trehalase activity in the supernatant of the fermentation solution was 1176 U/ml.

The supernatant of the shake flask culture fermentation solution of the trehalase MYC37 high expression strain ANMYC37 was taken and subjected to protein electrophoresis (SDS-PAGE). It was observed that the molecular weight of trehalase MYC37 was about 90 kDa, and the trehalase activity in the supernatant of the fermentation solution was 682 U/ml.

The supernatant of the shake flask culture fermentation solution of the trehalase TEM65 high expression strain ANTEM65 was taken and subjected to protein electrophoresis (SDS-PAGE). It was observed that the molecular weight of trehalase TEM65 was about 120 kDa, and the trehalase activity in the supernatant of the fermentation solution was 1488 U/ml.

Example 5 Analysis of the Enzymatic Properties of Trehalase (1) The protein concentration was measured by the Coomassie brilliant blue method (Bradford 1976).

The specific activity of trehalase THI37 was 184.03 U/mg, the specific activity of trehalase MYC37 was 166.73 U/mg, and the specific activity of trehalase TEM65 was 310.13 U/mg.

The trehalase gene Ms37 is derived from *Myceliophthora sepedonium*, and has the sequence of SEQ ID NO: 9, referring to patent WO2016205127. The trehalase gene Tr65 is derived from *Trichoderma reesei*, and has the sequence of SEQ ID NO: 10, referring to patent WO2013148993. The trehalases Ms37 and Tr65 expressed in *Aspergillus niger* according to the methods of Examples 1 and 2 were used as controls and compared with the three trehalases in the method. The specific activity of the trehalase Ms37 was 207.23 U/mg, and the specific activity of the trehalase Tr65 was 361.06 U/mg.

(2) Analysis on Optimum Temperature of Trehalase

The enzyme activity of the above different trehalase solutions was measured at 25° C., 30° C., 37° C., 50° C., 60° C., 70° C., and 80° C., respectively, using the trehalase activity measuring method. Three replicates were set for each sample, and the temperature corresponding to the highest point of enzyme activity is the optimum reaction temperature of the enzyme.

As shown in Table 2, the optimum reaction temperature of trehalase THI37 is 50° C., the optimum reaction temperature of trehalase MYC37 is 60° C., and the optimum reaction temperature of trehalase TEM65 is 60° C. Compared with the trehalases Ms37 and Tr65, the trehalases THI37, MYC37 and TEM65 have a wider temperature adaptation range and better temperature suitability.

TABLE 2

Analysis on optimum temperature of different trehalases
Relative enzyme activity %

| Trehalase | Temperature °C. | | | | | | |
|---|---|---|---|---|---|---|---|
| | 25 | 30 | 37 | 50 | 60 | 70 | 80 |
| THI37 | 28.78 | 39.47 | 62.61 | 100.00 | 91.39 | 11.42 | 5.93 |
| MYC37 | 5.58 | 8.37 | 17.93 | 57.37 | 100.00 | 40.64 | 5.18 |
| TEM65 | 10.48 | 18.31 | 39.08 | 94.89 | 100.00 | 47.10 | 4.31 |
| Ms37 | 8.93 | 12.95 | 24.76 | 72.75 | 100.02 | 12.05 | 9.84 |
| Tr65 | 20.89 | 23.11 | 55.10 | 100.00 | 43.11 | 3.56 | 2.22 |

(3) Determination of Temperature Stability of Trehalase

The above different trehalase solutions were subjected to heat preservation at 32° C., 37° C., and 60° C. for 1 hour, 2 hours, 3 hours, 4 hours, 6 hours, 16 hours, 24 hours, 30 hours, 48 hours, 54 hours, and 72 hours respectively, and then the enzyme activity was measured according to the above trehalase activity measuring method. Three replicates were set for each sample, and the thermal stability curves of the enzymes were drawn with the enzyme solution not subjected to heat preservation as a control.

Figure 2A:
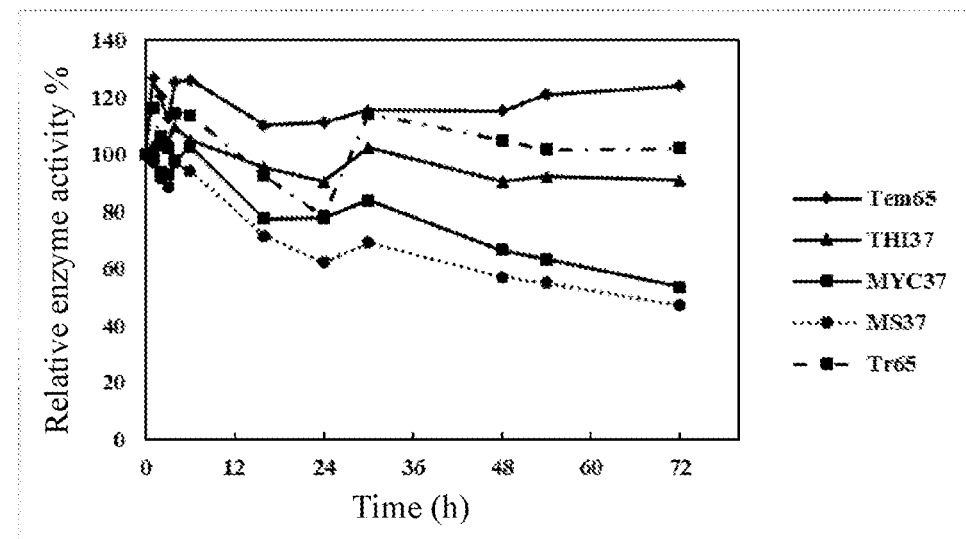
FIG. 2A Stability of trehalase at 32° C.
Figure 2B:
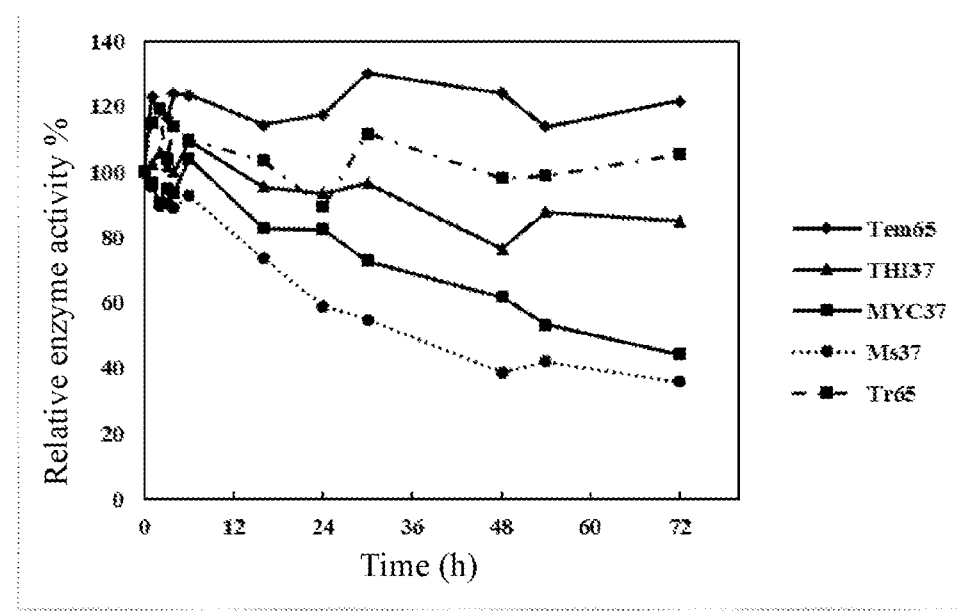
FIG. 2B Stability of trehalase at 37° C.
Figure 2C:
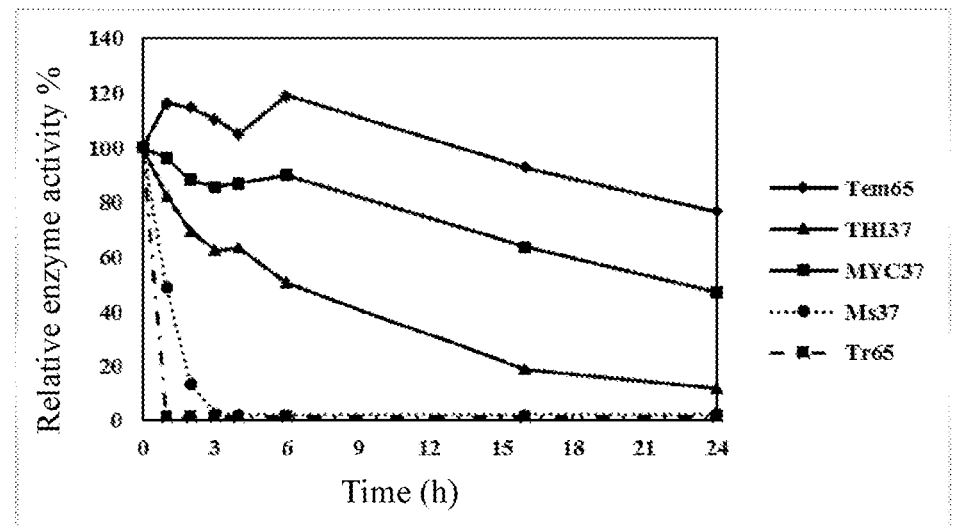
FIG. 2C Stability of trehalase at 60° C.

The results are shown in FIG. 2: The relative enzyme activity of the trehalases THI37, MYC37 and TEM65 is higher than that of the trehalase Ms37 within the same time of heat preservation at 32° C., 37° C. and 60° C., indicating that the trehalases THI37, MYC37 and TEM65 are more stable than Ms37 under different temperature conditions.

(4) Determination of Optimum pH of Trehalase

Buffers with different pH (pH of 2.5, 3.0, 3.5, 4, 4.5, 5.0, 5.5, 6, 6.5, 7, 7.5, and 8 respectively) were prepared, and the above trehalase solutions were diluted with the buffers with different pH to an appropriate concentration to obtain trehalase diluents with different pH. By the above trehalase activity measuring method, the enzyme activity in buffers with different pH was measured, and the relative enzyme activity curve was drawn.

As shown in Table 3, the optimum reaction pH of trehalase THI37 is 4.5, the optimum reaction pH of trehalase MYC37 is 4.0, and the optimum reaction pH of trehalase TEM65 is 5.0. Compared with the trehalase Ms37, the trehalases THI37, MYC37 and TEM65 have a wider pH adaptation range and better pH adaptability.

TABLE 3

Analysis on optimum pH of different trehalases
Relative enzyme activity %

| Trehalase | pH | | | | | | | | | | | |
|---|---|---|---|---|---|---|---|---|---|---|---|---|
| | .5 | .0 | .5 | .0 | .5 | .0 | .5 | .0 | .5 | .0 | .5 | .0 |
| THI37 | 2.42 | 0.09 | 6.68 | 1.03 | 00.00 | 6.41 | 2.38 | 7.58 | 2.33 | 9.46 | 6.14 | .48 |
| MYC37 | 3.33 | 5.76 | 1.82 | 00.00 | 1.72 | 9.49 | 6.37 | 3.31 | 3.33 | 4.34 | 5.36 | 7.27 |
| TEM65 | 1.13 | 2.12 | 5.19 | 0.00 | 7.21 | 00.00 | 9.49 | 2.63 | 5.01 | 8.16 | .79 | .13 |
| Ms37 | 4.88 | 0.47 | 4.00 | 00.00 | 0.23 | 7.44 | 8.14 | 9.96 | 4.16 | 6.05 | 7.91 | 0.93 |
| Tr65 | 5.57 | 9.08 | 9.98 | 9.00 | 6.82 | 5.00 | 1.82 | 9.51 | 2.48 | 4.08 | 9.24 | .36 |

(5) Measurement of pH Stability

The trehalase solutions were diluted with a buffer with pH 4.0 to an appropriate concentration, and the diluents were subjected to heat preservation at 32° C. for 2 hours, 6 hours, 24 hours, 48 hours, 54 hours, and 72 hours, and the enzyme activity was measured by the above trehalase activity measuring method. Three replicates were set for each sample, and the pH stability curve was drawn.

Figure 3:
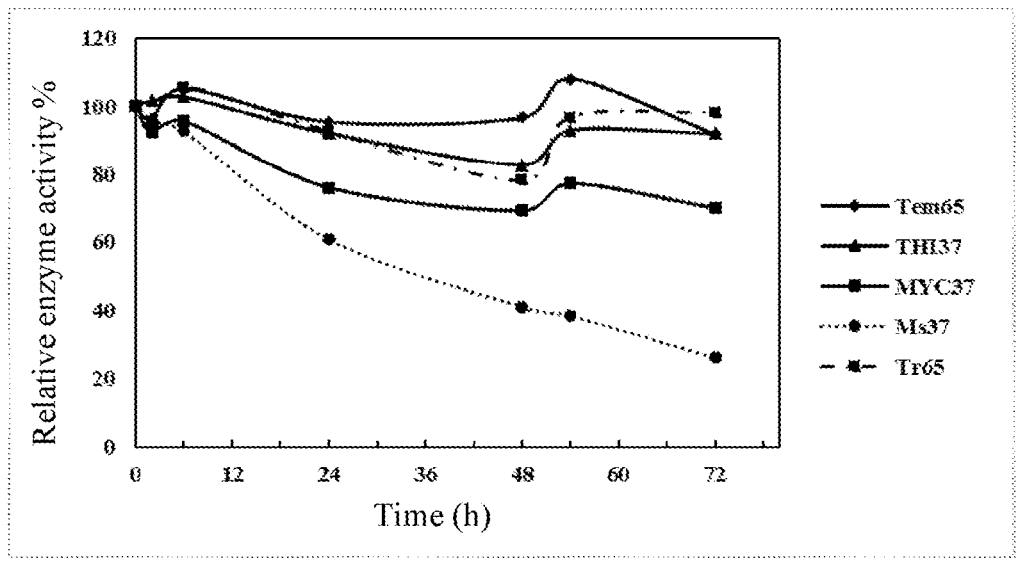
FIG. 3 Stability of trehalase at pH 4.0.

The results are shown in FIG. 3: The relative enzyme activity of the trehalases THI37, MYC37 and TEM65 is all higher than that of trehalase Ms37 within the same time of heat preservation at pH 4.0, indicating that under the condition, the trehalases THI37, MYC37 and TEM65 are more stable than Ms37.

Example 6 Addition of Trehalase to Fermentation Supernatant at the End of Alcohol Fermentation Alcohol mature mash from an alcohol production factory was centrifuged and the supernatant was taken. The trehalose content in the supernatant was determined as 2,551 mg/L by ion chromatography. An appropriate amount of the supernatant was taken, the pH of the supernatant was adjusted to 4.0, and the supernatant was dispensed into 5 ml centrifuge tubes. The amount of the supernatant in each centrifuge tube was 3 ml. The trehalase Tr65 expressed in Aspergillus niger according to the methods of Examples 1 and 2 was used as a control and added into the centrifuge tubes together with the three trehalases in the disclosure respectively, at an added amount of 0.2 U/g DS. The control group was not added with trehalase. Reaction conditions were: 32° C., 18 h. At the end of the reaction, the enzyme was inactivated in a boiling water bath for 10 min, and then the trehalose content was detected by ion chromatography. As shown by the experimental results in Table 4, the trehalase THI37 has the best hydrolysis effect on trehalose in alcohol mature mash, and is significantly better than the trehalase Tr65. At the end of the reaction, the trehalase THI37 can hydrolyze 100% of trehalose in the fermentation solution. The trehalases MYC37 and TEM65 have significantly better hydrolysis effect on the trehalose in the alcohol mature mash than the trehalase Tr65, and at the end of the reaction, could hydrolyze 91.7% and 92.6% of the trehalose in the fermentation solution, respectively.

TABLE 4

Ion chromatography analysis results of alcohol mature mash

| Trehalase | Added amount (U/g) | Trehalose (mg/L) | Trehalose hydrolysis rate (%) |
|---|---|---|---|
| Control | 0 | 2551 | 0 |
| Tr65 | 0.2 | 498 | 80.5 |
| THI37 | 0.2 | 0 | 100.0 |

TABLE 4-continued

Ion chromatography analysis results of alcohol mature mash

| Trehalase | Added amount (U/g) | Trehalose (mg/L) | Trehalose hydrolysis rate (%) |
|---|---|---|---|
| MYC37 | 0.2 | 212 | 91.7 |
| TEM65 | 0.2 | 188 | 92.6 |

Example 7 Effect of Addition of Trehalase on Corn Starch Alcohol Fermentation Liquefaction of an alcohol fermentation raw material: A certain amount of ground corn flour (purchased from an alcohol factory) was taken to prepare a slurry with a material-water ratio of 1:2.3. After the preparation, the pH was adjusted to 5.6, and an appropriate amount of thermostable amylase (BaiLiChun X5) was added (the added amount was 10-100 U/g DS) for performing liquefaction. Liquefaction conditions were: temperature 95° C., time 120 min.

Alcohol fermentation: The liquefied slurry was cooled to room temperature in time and the pH was adjusted to 4.3 (the pH was adjusted with a 1 mol/L hydrochloric acid or 3 mol/L sodium hydroxide solution). The slurry was dispensed evenly into shake flasks, and 50-500 U/g DS complex saccharifying enzyme (Bestzyme HighDEX ultra), 200-1000 ppm active dry yeast (highly active dry yeast for brewing, purchased from Angel Yeast Co., Ltd.), and 600 ppm nitrogen source urea were added for performing corn alcohol fermentation. The experimental group was added with trehalase at the beginning of fermentation, and the added amount of the enzyme was 0.5 U/g DS. The control group was not added with trehalase. The fermentation conditions were: temperature 32° C., time 72 h. At the end of the fermentation, the content of ethanol and other components in the fermentation solution was detected by high performance liquid chromatography, and another part of the mash was taken to measure the residual total sugar. As shown by the experimental results in Table 5, the addition of trehalase in the fermentation process could help increase the yield of alcohol, wherein trehalase THI37 had the best effect, the alcohol yield was increased by 1.43% compared with the control group without addition of trehalase, and the residual total sugar concentration was significantly reduced at the end of fermentation. The effect of adding the trehalase TEM65 was equivalent to that of trehalase Tr65, and compared with the control group without addition of trehalase, the alcohol yield was increased by 1.29%, and the residual total sugar concentration was significantly reduced at the end of fermentation.

Addition of trehalase in the pre-saccharification process (start, middle and end) of fermentation, in the yeast fermentation process (start, middle and end), and in the simultaneous fermentation and saccharification process (start, middle and end) can increase the yield of alcohol, and reduce the residual total sugar concentration at the end of fermentation.

TABLE 5

HPLC analysis results of alcohol fermentation solution

| Trehalase | Added amount (U/g) | Disaccharide % (w/v) | Glucose % (w/v) | Residual total sugar % (w/v) | Alcohol % (v/v) |
|---|---|---|---|---|---|
| Control | 0 | 0.33 | 0.14 | 2.90 | 14.73 |
| Tr65 | 0.5 | 0.27 | 0.14 | 2.61 | 14.91 |
| THI37 | 0.5 | 0.27 | 0.14 | 2.05 | 14.94 |
| MYC37 | 0.5 | 0.27 | 0.13 | 2.25 | 14.89 |
| TEM65 | 0.5 | 0.27 | 0.14 | 2.50 | 14.92 |

Example 8 Addition of Trehalase to the Fermentation Supernatant at the End of Glutamic Acid Fermentation A glutamic acid fermentation solution from a factory was centrifuged and the supernatant was taken. The trehalose content in the supernatant was determined as 4,504 mg/L by ion chromatography. An appropriate amount of the supernatant was taken and dispensed into 5 ml centrifuge tubes. The amount of the supernatant in each centrifuge tube was 3 ml. 4 types of different trehalases were added to the centrifuge tubes respectively, and the added amount was 0.5 U/ml supernatant. The reaction conditions were: pH 6.8, temperature 37° C., and reaction time 5 h. After the end of the reaction, the trehalose content was detected by ion chromatography. As shown by the experimental results in Table 6, the trehalase THI37 has the best hydrolysis effect on trehalose in the glutamic acid fermentation solution, and is significantly better than the trehalase Tr65. At the end of the reaction, the trehalase THI37 can hydrolyze 91.0% of trehalose in the fermentation solution. Addition of trehalase in the glutamic acid fermentation process could also help degrade trehalose in the fermentation solution and improve sugar utilization.

TABLE 6

Ion chromatography analysis results of glutamic acid fermentation solution

| Trehalase | Added amount (U/g) | Trehalose (mg/L) | Trehalose hydrolysis rate (%) |
|---|---|---|---|
| Control | 0 | 4504 | 0 |
| Tr65 | 0.5 | 3000 | 33.4 |
| THI37 | 0.5 | 407 | 91.0 |
| MYC37 | 0.5 | 3307 | 26.6 |
| TEM65 | 0.5 | 3933 | 12.7 |

Example 9 Addition of Trehalase to the Fermentation Supernatant at the End of Lysine Fermentation A lysine fermentation solution from a factory was centrifuged and the supernatant was taken. The trehalose content in the supernatant was determined as 5427 mg/L by ion chromatography. An appropriate amount of the supernatant was taken and dispensed into 5 ml centrifuge tubes. The amount of the supernatant in each centrifuge tube was 3 ml. 5 types of different trehalases were added to the centrifuge tubes respectively, and the added amount was 0.5 U/ml supernatant. The reaction conditions were: pH 7.39, temperature 37° C., and reaction time 5 h. After the end of the reaction, the trehalose content was detected by ion chromatography. As shown by the experimental results in Table 7, the trehalase MYC37 has the best hydrolysis effect on trehalose in the lysine fermentation solution, and is significantly better than the trehalase Tr65. At the end of the reaction, the trehalase MYC37 can hydrolyze 88.1% of trehalose in the fermentation solution. The trehalases THI37 has a significantly better hydrolysis effect on the trehalose in the lysine fermentation solution than the trehalase Tr65. Addition of trehalase in the lysine fermentation process could also help degrade trehalose in the fermentation solution and improve sugar utilization.

TABLE 7

Ion chromatography analysis results of lysine fermentation solution

| Trehalase | Added amount (U/g) | Trehalose (mg/L) | Trehalose hydrolysis rate (%) |
|---|---|---|---|
| Control | 0 | 5427 | 0 |
| Tr65 | 0.5 | 5139 | 5.3 |
| THI37 | 0.5 | 3888 | 28.4 |
| MYC37 | 0.5 | 648 | 88.1 |
| TEM65 | 0.5 | 5080 | 6.4 |

What is claimed is:

1. A method for producing a fermented product comprising an alcohol, wherein the method comprises:
(a) adding amylase to liquefy an alcohol fermentation raw material;
(b) saccharifying the liquefied raw material;
(c) adding yeast and performing fermentation;
(d) collecting alcohol mature mash supernatant after the end of fermentation; and
(e) adding a polypeptide with trehalase activity to the alcohol mature mash supernatant at an amount of 0.05-10 U/g DS to produce the fermented product, wherein the polypeptide comprises at least 95% sequence identity to the polypeptide of SEQ ID NO: 6.

2. The method according to claim 1, wherein step (b) comprises adding a saccharifying enzyme, and step (c) further comprises adding a nitrogen source.

3. A method for producing a fermented product comprising an amino acid, wherein the method comprises:
(a) culturing a seed solution of fermentation microbes;
(b) performing fermentation;
(c) collecting a fermentation solution; and
(d) adding a polypeptide with trehalase activity to the fermentation solution at a concentration of 0.05-5 U/ml and reacting the fermentation solution comprising the polypeptide with trehalase activity at about 37° C., for about 5 hours, at about pH 6.8 to produce the fermented product, wherein the polypeptide comprises at least 95% sequence identity to the polypeptide of SEQ ID NO: 6.

4. The method according to claim 1, wherein the polypeptide with trehalase activity comprises at least 97% sequence identity to the polypeptide of SEQ ID NO: 6.

5. The method according to claim 1, wherein the method further comprises pre-saccharifying the liquefied material before step (b), wherein the polypeptide with trehalase activity can be present or added in the pre-saccharifying the liquefied material before step (b).

6. The method according to claim 1, wherein the polypeptide with trehalase activity is added to the alcohol mature mash supernatant at an amount of about 0.2-0.5 U/g DS.

7. The method according to claim 6, wherein step (e) further comprises reacting the alcohol mature mash supernatant comprising the polypeptide with trehalase activity at about 32° C. for about 18 hours, and the polypeptide with trehalase activity comprises at least 98% sequence identity to the polypeptide of SEQ ID NO: 6.

8. The method according to claim 7, wherein the polypeptide with trehalase activity is added to the alcohol mature mash supernatant at an amount of about 0.2 U/g DS.

9. The method according to claim 1, wherein the polypeptide with trehalase activity is present during step (c).

10. The method according to claim 3, wherein the polypeptide with trehalase activity comprises at least 97% sequence identity to the polypeptide of SEQ ID NO: 6.

11. The method according to claim 3, wherein the amino acid is glutamic acid, lysine, threonine, valine, proline, tryptophan, isoleucine or leucine.

12. The method according to claim 11, wherein the amino acid is glutamic acid or lysine.

13. The method according to claim 3, wherein the fermentation solution consists of amino acid fermentation solution supernatant.

14. The method according to claim 13, wherein the polypeptide with trehalase activity is added to the fermentation solution at a concentration of 0.3-1 U/ml.

15. The method according to claim 14, wherein the polypeptide with trehalase activity comprises at least 98% sequence identity to the polypeptide of SEQ ID NO: 6.

16. The method according to claim 15, wherein the polypeptide with trehalase activity is added to the fermentation solution at a concentration of about 0.5 U/ml.

17. The method of claim 3, wherein the polypeptide with trehalase activity is present during step (b).

18. The method according to claim 1, wherein the polypeptide with trehalase activity comprises at least 99% sequence identity to the polypeptide of SEQ ID NO:6.

19. The method according to claim 1, wherein the polypeptide with trehalase activity comprises the polypeptide of SEQ ID NO: 6.

20. The method according to claim 3, wherein the polypeptide with trehalase activity comprises at least 99% sequence identity to the polypeptide of SEQ ID NO:6.

* * * * *